United States Patent [19]

Kao et al.

[11] Patent Number: 5,411,967
[45] Date of Patent: May 2, 1995

[54] CARBAMATES OF RAPAMYCIN

[75] Inventors: Wenling Kao, Paoli, Pa.; Jerauld S. Skotnicki, Allentown, N.J.; Magid A. Abou-Gharbia, Glen Mills; Yvette L. Palmer, Newtown, both of Pa.

[73] Assignee: American Home Products Corporation, Madison, N.J.

[21] Appl. No.: 224,893

[22] Filed: Apr. 8, 1994

Related U.S. Application Data

[60] Continuation-in-part of Ser. No. 160,984, Dec. 1, 1993, abandoned, which is a division of Ser. No. 54,655, Apr. 23, 1993, Pat. No. 5,302,584, which is a continuation-in-part of Ser. No. 960,597, Oct. 13, 1992, abandoned.

[51] Int. Cl.$^6$ ............... C07D 491/06; A61K 31/675; A61K 31/395
[52] U.S. Cl. ..................... 514/291; 514/63; 540/452; 540/456
[58] Field of Search .................. 514/291, 63; 540/452, 540/456

[56] References Cited

U.S. PATENT DOCUMENTS 5,118,678  6/1992  Kao et al. ........................ 514/183
5,302,584  4/1984  Kao et al. ........................ 514/291

Primary Examiner—Robert T. Bond
Attorney, Agent, or Firm—Arnold S. Milowski

[57] ABSTRACT

A compound of the structure

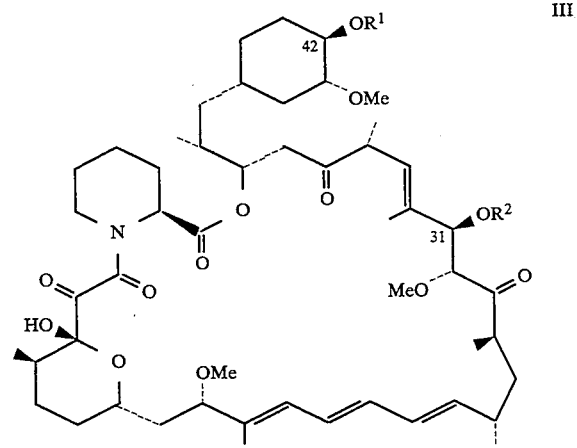

where the substituents are defined in the main body of the specification which is useful as an immunosuppressive, antiinflammatory, antifungal, antiproliferative, and antitumor agent.

36 Claims, No Drawings

CARBAMATES OF RAPAMYCIN

CROSS-REFERENCE TO RELATED APPLICATIONS

This application is a continuation in part of Ser. No. 08/160,984, filed Dec. 1, 1993, now abandoned, which is a divisional of Ser. No. 08/054,655; filed Apr. 23, 1993, now U.S. Pat. No. 5,302,584, which is a continuation in part of Ser. No. 07/960,597, filed Oct. 13, 1992 now abandoned.

BACKGROUND OF THE INVENTION

This invention relates to carbamates of rapamycin and a method for using them for inducing immunosuppression, and in the treatment of transplantation rejection, graft vs. host disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, antiinflammatory, antifungal, and antitumor agents.

DESCRIPTION OF THE INVENTION

This invention provides derivatives of rapamycin which are useful as immunosuppressive, antiinflammatory, antifungal, antiproliferative, and antitumor agents having the structure

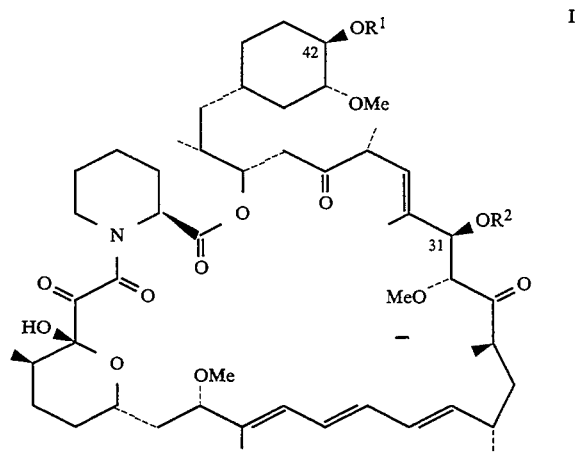

wherein $R^1$ and $R^2$ are each, independently, hydrogen, $-CONH-[(CR^3R^4)_m(-A-(CR^5R^6)_n)_p]_q-B$;

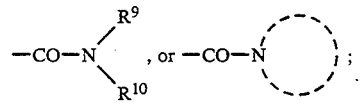

$R^3$, $R^4$, $R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-OR^7$, $-SR^7$, halogen, $-CN$, $-NO_2$, $-CF_3$, $-COR^7$, $-CO_2R^7$, $-CONHR^7$, $-SO_2R^7$, $SO_2R^7$, $-OSO_3R^7$, $-NR^7R^8$, $-NHCOR^7$, $-NHSO_2R^7$, or Ar;

$R^7$ and $R^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^9$ and $R^{10}$ are each, independently, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-CF_3$, $-COR^7$, $-CO_2R^7$, $-CONHR^7$, $-SO_2R^7$, or Ar;

A is $-CH_2-$, $-NR^7-$, $-O-$, $-S-$, $-SO-$, $-SO_2-$, $-PR^7-$, $-CO-$, $-NHCO-$, $-NHSO-$, or $-P(O)(R^7)-$;

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b]thiophenolyl, benzimidazolyl, benzthiazolyl, enzodioxolyl, piperidinyl, morpholinyl, piperazinyl, tetrahydrofuranyl, or pyrrolidinyl; wherein the Ar group may be optionally mono-, di-, or tri-substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —$SO_3H$, —$PO_3H$, and —$CO_2H$;

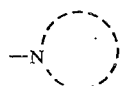

is a nitrogen containing heterocycle that may be saturated, unsaturated, or partially unsaturated, and may be optionally mono-, di-, or tri- substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —$SO_3H$, —$PO_3H$, and —$CO_2H$;

with the proviso that $R^1$ and $R^2$ are not both hydrogen;
m=0-6;
n=0-6;
p=0-1;
q=0-1;
or a pharmaceutically acceptable salt thereof.

The pharmaceutically acceptable salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the aryl portion of the arylalkyl substituent is a phenyl, piperazinyl, piperidinyl, or pyridyl group that is optionally mono-, di-, or trisubstituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —$SO_3H$, —$PO_3H$, and —$CO_2H$. The term alkyl includes both straight chain and branched alkyl groups.

It is preferred that

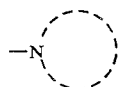

is a pyridyl, pyrazinyl, piperidinyl, morpholinyl, piperazinyl, pyrrolidinyl, thiazolyl, pyrimidinyl, isoxazolyl, pyrrolidinyl, or imidazolyl group that may be optionally substituted as described above.

Of these compounds, preferred members are those having the structure

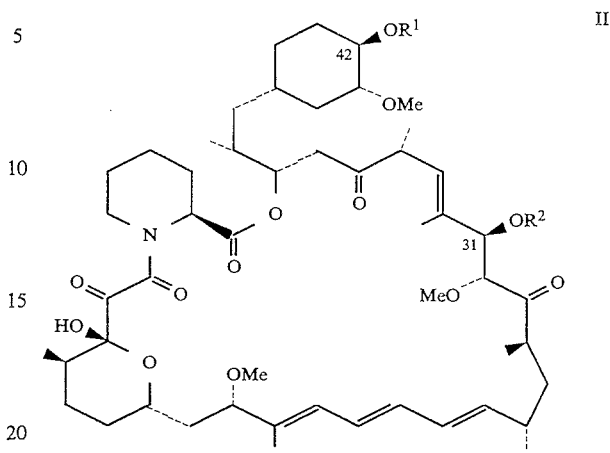

wherein $R^1$ and $R^2$ are each, independently, hydrogen, or —CONH—[$(CR^3R^4)_m$(—A—$(CR^5 R^6)_n)_p]_q$—B;

$R^3$, $R^4$, $R^5$, $R^6$, and B are each, independently, hydrogen, alkyl of 1-6 carbon atoms, arylalkyl of 7-10 carbon atoms, cycloalkyl of 3-8 carbon atoms, —$OR^7$, —$SR^7$, halogen, —CN, —$NO_2$, —$CF_3$, —$COR_7$, —$CONH_2$, —$SO_2R_7$, —$OSO_3R^7$, —$NR^7R^8$, —$NHCOR^7$, —$NHSO_2R^8$, or Ar;

A is —$CH_2$—, —$NR^7$—, —O—, —S—, —$SO_2$—, —$PR^7$—, or —$P(O)(R^7)$—;

$R^7$ and $R^8$ are each, independently, hydrogen, alkyl of 1-6 carbon atoms, arylalkyl of 7-10 carbon atoms, or Ar;

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri- substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —$SO_3H$, —$PO_3H$, and —$CO_2H$;

with the proviso that $R^1$ and $R^2$ are not both hydrogen;
m=0-6;
n=0-6;
p=0-1;
q=0-1;
or a pharmaceutically acceptable salt thereof.

Preferred members also include those compounds in which $R^2$ is hydrogen; those in which p=0 and B is Ar; those in which p=0, B is Ar, and $R^2$ is hydrogen; those in which p=0, B is Ar, $R^2$ is hydrogen, and Ar is pyridyl, furyl, piperazinyl, piperazinyl, and piperidinyl; those in which m=0-3 and p=0; those in which m=2, n=0, p=1, q=1 and A is —O— or $NR^7$; those in which $R^1$ is

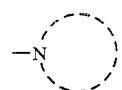

and $R^2$ is hydrogen; and those in which $R^1$ is

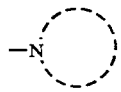

$R^2$ is hydrogen, and

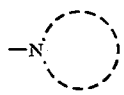

is an optionally substituted morpholinyl or piperazinyl group.

This invention also discloses preferred compounds having the structure

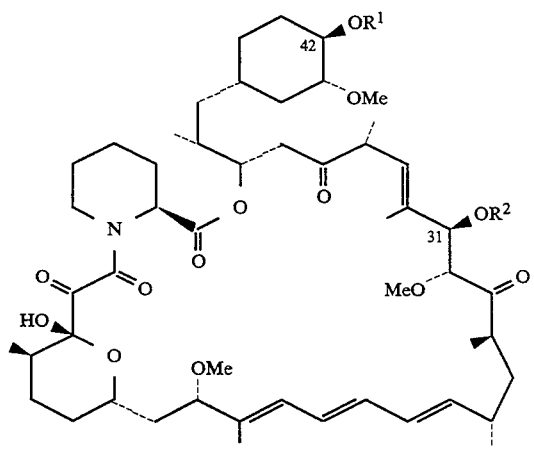

III wherein $R^1$ and $R^2$ are each, independently, hydrogen, —CONH—A—$(CR^5R^6)_n$—B, —$CONR^{11}$—A—$(CR^5R^6)_n$—B,

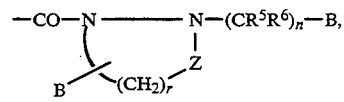

or 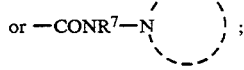 ;

$R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —$OR^7$, —$SR^7$, halogen, —CN, —$NO_2$, —$CF_3$, —$COR^7$, —$CO_2R^7$, —$CONHR^7$, —$SO_2R^7$, —$OSO_3R^7$, —$NR^7R^8$, —$NHCOR^7$, —$NHSO_2R^7$, —$SO_2NR^7R^8$, or Ar;

$R^7$ and $R^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^{11}$ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —$NR^7$, —NHCO—, —N═C—, or —NHSO—;

Z is —$CH_2$— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3,-dihydroisobenzofuran-5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benz[b]-thiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —$SO_3H$, and —$CO_2H$;

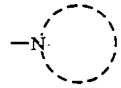

is a nitrogen containing heterocycle that may be saturated, unsaturated, or partially unsaturated, and may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, and —$CO_2H$;

n=0–6;

r=1–4;

with the proviso that $R^1$ and $R^2$ are not both hydrogen and further provided that when n=0, B is not —$NR^7R^8$, —$NHCOR^7$, —N═C—, or —$NHSO_2R^7$; or a pharmaceutically acceptable salt thereof.

For the compounds having the structure III (immediately above) the definition of arylalkyl, alkyl, and of the pharmaceutically acceptable salts is the same as was defined following the compounds of structure I. The aryl radical in the arylsulfonamido and arylsulfonyl moieties are as defined for arylalkyl. A carbamyl radical is defined as —CONH$_2$, and an alkylcarbamyl radical is defined as —CONH-alkyl. An aminosulfonyl radical is defined as —SO$_2$NH$_2$, and an alkylaminosulfonyl radical is defined as —SO$_2$NH-alkyl. An alkylsulfonyl radical group is defined as —SO$_2$-alkyl.

It is preferred that

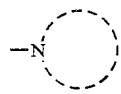

is a piperidinyl, piperazinyl, morpholinyl, pyrrolidinyl, or imidazolyl group that may be optionally substituted as described above.

Of the compounds having structure III, preferred members include those in which R$^2$ is hydrogen; those in which R$^2$ is hydrogen and R$^1$ is —CONH—A—(CR$^5$R$^6$)$_n$—B; those in which R$^2$ is hydrogen, R$^1$ is —CONH—A—(CR$^5$R$^6$)$_n$—B, and B is Ar; those in which R$^2$ is hydrogen, R$^1$ is —CONH—A—(CR$^5$R$^6$)$_n$—B, B is Ar, and n is 0; those in which R$^2$ is hydrogen, R$^1$ is —CONH—A—(CR$^5$R$^6$)$_n$—B, B is Ar, n is 0, and A is NR$^7$; those in which R$^2$ is hydrogen and R$^1$ is

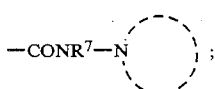

and those in which R$^2$ is hydrogen, R$^1$ is

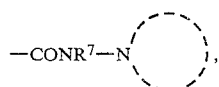

R$^7$ is hydrogen, and

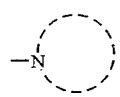

is piperidinyl or piperazinyl.

The compounds of this invention carbamylated at the 42-position or at both the 31- and 42-positions can be prepared by converting the 42- and/or 31-alcohols of rapamycin to a carbonate followed by reaction with an appropriately substituted amine or hydrazine to provide the desired carbamate. As shown below, and in the Examples, the carbazates having a free terminal amino group can be further reacted with suitable electrophiles to provide substituted carbazates, such as the compound of Example 30. The following scheme illustrates the preparation of the compounds of Examples 2, 30, and 38.

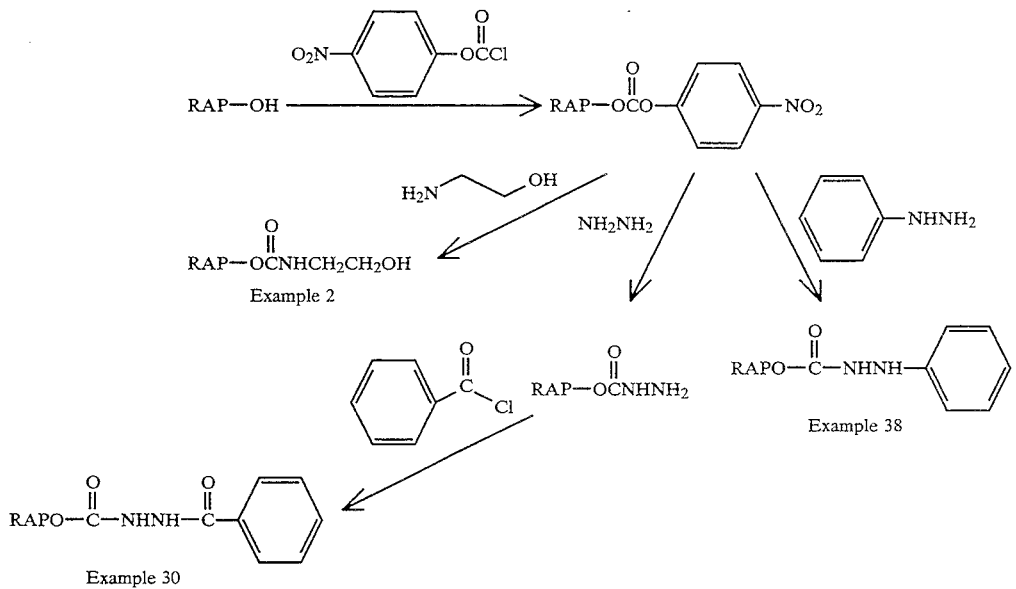

Alternatively, the compounds of this invention carbamylated at the 42-position or at both the 31- and 42-positions can be prepared by reacting rapamycin with an appropriately substituted isocyanate under neutral conditions or in the presence of a base, such as pyridine. Preparation of carbamates of rapamycin using this method was disclosed in U.S. Pat. No. 5,118,678, which is hereby incorporated by reference.

The 31-carbamylated compounds of this invention can be prepared by protecting the 42-alcohol of rapamycin with a protecting group, such as with a tert-butyl dimethylsilyl group, followed by carbamylation of the 31-position by the procedures described above. Removal of the protecting group provides the 31-carbamylated compounds. In the case of the tert-butyl dimethylsilyl protecting group, deprotection can be accomplished under mildly acidic conditions.

Having the 31-position carbamylated and the 42-position deprotected, the 42-position can be carbamylated using a different amine (via the carbonate) or isocyanate than was reacted with the 31-alcohol, to give compounds having different carbamates at the 31- and 42-positions. Alternatively, the 42-carbamylated compounds, prepared as described above, can be reacted with a different amine (via the carbonate) or isocyanate to provide compounds having different carbamates at the 31- and 42-positions.

The amines and isocyanates used to prepare the compounds of the invention are commercially available or can be prepared by methods that are disclosed in the literature.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 42-oxorapamycin [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxy- and 15,27-bishydroxy-rapamycin [U.S. Pat. No. 5,102,876]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 2.2–9.9 nM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{{}^3H\text{-control thymus cells} - {}^3H\text{-rapamycin-treated thymus cells}}{{}^3H\text{-control thymus cells} - {}^3H\text{-test compound-treated cells}}$$

Representative compounds of this invention were also evaluated in an in vivo test procedure designed to determine the survival time of pinch skin graft from male BAB/c donors transplanted to male C3H(H—2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. The following table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 12.0±1.7 days was obtained for rapamycin at 4 mg/kg.

The following table summarizes the results of representative compounds of this invention in these two standard test procedures.

TABLE 1

| | EVALUATION OF IMMUNOSUPPRESSIVE ACTIVITY* | | |
|---|---|---|---|
| | LAF | | Skin Graft |
| Compound | $IC_{50}$ (nM) | (ratio) | (days ± SD) |
| Example 1 | 1.7 | 1.29 | 11.7 ± 0.5 |
| Example 2 | 1.8 | 1.22 | 10.3 ± 0.8 |
| | 4.4 | 1.09 | |
| Example 3 | 6.5 | 0.34 | |
| Example 4 | 10.0 | 0.45 | 9.8 ± 0.8 |
| Example 5 | 2.1 | 1.19 | |
| Example 6 | 0.8 | 5.1 | 11.40 ± 0.6 |
| Example 7 | 1.2 | 2.3 | 10.33 ± 0.5 |
| Example 8 | 0.2 | 4.4 | |
| Example 10 | 0.1 | 3.8 | 10.17 ± 1.0 |
| Example 11 | 0.7 | 5.0 | 11.40 ± 0.9 |
| Example 12 | 1.1 | 3.8 | 9.80 ± 1.1 |
| Example 13 | 0.9 | 3.8 | 9.50 ± 0.6 |
| Example 14 | 0.5 | 3.8 | 9.17 ± 1.7 |
| Example 21 | 6.0 | 0.6 | 10.4 ± 0.5 |
| Example 23 | 3.4 | 1.4 | |
| Example 24 | 40.0 | 0.1 | |
| Example 26 | 0.2 | 6.2 | |
| Example 27 | 1.2 | 1.2 | |
| Example 28 | 4.2 | 1.1 | |
| Example 29 | 2.6 | 0.58 | |
| Example 30 | 2.2 | 0.68 | |
| Example 33 | 4.8 | 0.16 | |
| Example 34 | 0.3 | 3.00 | |
| | 1.0 | 1.10 | |
| Example 36 | 2.3 | 0.24 | |
| Example 38 | 0.05 | 22.0 | 11.0 ± 0.6 |
| | 0.3 | 2.67 | |
| Exwnple 39 | 0.3 | 3.00 | |
| Example 41 | 0.8 | 0.62 | |
| Example 42 | 0.3 | 3.00 | |
| Example 43 | 0.5 | 1.80 | |
| Example 44 | 1.1 | 0.73 | |
| | 0.7 | 0.85 | |
| | 3.0 | 0.53 | |
| Example 45 | 1.0 | 1.09 | |
| Example 46 | 0.5 | 1.80 | 10.0 ± 0.9 |
| | 0.3 | 2.34 | |
| Example 47 | 5.3 | 0.18 | 10.1 ± 0.4 |
| | | | 9.2 ± 1.0 |
| Example 48 | 0.3 | 2.5 | |
| Example 49 | 1.6 | 0.56 | |
| Example 50 | 27.0 | 0.04 | |

*Calculation of the ratio was described supra.

The results of these standard pharmacological test procedures demonstrate immunosuppressive activity both in vitro and in vivo for the compounds of this invention. Positive ratios in the LAF test procedures indicates suppression of T-cell proliferation, thereby demonstrating the immunosuppressive activity of the compounds of this invention. As transplanted pinch skin grafts are typically rejected within 6–7 days without the use of an immunosuppressive agent, the increased survival time of the skin graft when treated with the compounds of this invention further demonstrates their utility as immunosuppressive agents. Additionally, the results obtained in the skin graft test procedure further demonstrates the ability of the compounds of this invention to treat or inhibit transplantation rejection.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Based on the activity profile obtained in the standard pharmacological test procedures described above, the compounds of this invention also are considered to have antitumor, antifungal activities, and antiproliferative activities. The compounds of this invention therefore are also useful in treating solid tumors, fungal infections, and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive, antirejection, or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane coveting a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg–100 mg/kg, preferably between 0.001 –25 mg/kg, and more preferably between 0.01-5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

Rapamycin 42-ester with carbamic acid

A solution of 2.0 g of rapamycin in 10 ml of dichloromethane and 2 mL of dry pyridine was cooled to −78° C. under a nitrogen atmosphere. To this solution, 662 mg 4-nitrophenyl chloroformate was added; the resulting solution was stirred at room temperature under nitrogen for 20 hours. The mixture was diluted with water and extracted with dichloromethane. The dichloromethane extract was washed with water, dried over MgSO₄ and evaporated. The residue was chromatographed on silica gel. Elution with 33% ethyl acetate in n-hexane gave 2.07 g of rapamycin 42-p-nitrophenyl carbonate as a white foam.

A solution of 630 mg rapamycin 42-p-nitrophenyl carbonate in 25 mL dichloromethane was treated at 0° with ammonia gas for one hour. The resulting yellow suspension was filtered and the filtrate was evaporated. The residue was chromatographed on silica gel. Elution with 25% n-hexane in ethyl acetate afforded 430 mg of the title compound as a white foam, mp 101°-103°.

IR(KBr): 3450 (OH and NH), 1720 (lactone and ketone C=O), 1645 (amide C=O), 1460, 1190, 890, 760 cm⁻¹. ¹H NMR (CDCl₃, 400 MHz): δ4.6 (s, 2H, NH₂), 3.40, 3.33, 3.14 (all s, 3H, —OCH₃) ppm. MS (neg. ion FAB): 956 (M⁻), 590, 364.

EXAMPLE 2

Rapamycin 42-ester with 2-hydroxyethyl carbamic acid

A solution of 270 mg rapamycin 42-p-nitrophenyl carbonate in 8 mL dichloromethane was treated at −10° C. under a nitrogen atmosphere with 61 mg ethanolamine in 0.5 mL dichloromethane. The yellow solution was stirred at 0° C. under a nitrogen atmosphere for 45 minutes. The reaction mixture was diluted with 120 mL dichloromethane, washed with 1N HCl, water, dried with MgSO₄ and evaporated. The residue was chromatographed on silica gel. Elution with ethyl acetate/n-hexane (2/1) afforded 85 mg of the title compound as a white foam, mp 100°–105°.

IR(KBr): 3430 (OH, NH), 1720 (lactone and ketone C=O)), 1640 (amide C=O), 1520, 1450, 1240, 1080, 985 and 760 cm⁻¹. ¹H NMR (CDCl₃, 400 MHz): 3.70 (m, 2H, —CH₂—OH), 3.65 (m, 2H, —NH—CH₂), 3.38, 3.33, 3.14 (all s, 3H, —OCH₃) ppm. MS (neg ion FAB): 1000 (M⁻), 590, 408, 297.

The following representative compounds can be prepared from rapamycin 42-p-nitrophenyl carbonate (prepared as disclosed in Example 1 ) and the appropriate amine by employing the method used to prepare the title compound in Example 2.

Rapamycin 42 -ester with cyclohexyl carbamic acid
Rapamycin 42-ester with napthyl carbamic acid
Rapamycin 42-ester with 1-(2-naphthylethyl) carbamic acid
Rapamycin 42-ester with 3-cyanopropyl carbamic acid
Rapamycin 42-ester with 2-hydroxy-hexafluoroisopropyl carbamic acid
Rapamycin 42-ester with 2-methoxycarbonyl-2-(4-hydroxyphenyl)ethyl carbamic acid
Rapamycin 42-ester with 1-(2-hydroxyisoxazolyl)-methyl carbamic acid
Rapamycin 42-ester with 2-methoxyisopropyl carbamic acid
Rapamycin 42-ester with 2,2-dimethoxyethyl carbamic acid
Rapamycin 42-ester with 2-phosphonoxyethyl carbamic acid
Rapamycin 42-ester with 2-sulfinoethyl carbamic acid
Rapamycin 42-ester with 2-methoxyethyl carbamic acid
Rapamycin 42-ester with 1-carboxy-3-(methylsulfinyl)-propyl carbamic acid
Rapamycin 42-ester with 1-methoxycarbonyl-3-(methylthio)propyl carbamic acid
Rapamycin 42-ester with 1,3-(bis-ethoxycarbonyl)propyl carbamic acid
Rapamycin 42-ester with 1-ethoxycarbonyl-2-methylpropyl carbamic acid
Rapamycin 42-ester with 1-butoxycarbonyl-2-hydroxyethyl carbamic acid
Rapamycin 42-ester with 1-methoxycarbonyl-2-(4-hydroxyphenyl)ethyl carbamic acid
Rapamycin 42-ester with 1-methoxycarbonyl-2-(5-imidazolyl)ethyl carbamic acid
Rapamycin 42-ester with 1-(phenoxycarbonyl)methyl carbamic acid
Rapamycin 42-ester with 1-carboxy-2-methyl-2-phosphonoxyethyl carbamic acid
Rapamycin 42-ester with 1-carbophenylmethoxy-2-(phenylmethoxy)ethyl carbamic acid
Rapamycin 42-ester with 1-(4-bromopehnoxymethyl)ethyl carbamic acid
Rapamycin 42-ester with 2-(phenylcarbonyloxy)ethyl carbarnic acid
Rapamycin 42-ester with 1-propylcarbonyloxy-3-methylpropyl carbamic acid Rapamycin 42-ester with 1-phenylmethoxycarbonyl-3-(3-indolyl)propyl carbamic acid Rapamycin 42-ester with 1-propyloxycarbonyl-3-(methylsulfinyl)propyl carbamic acid Rapamycin 42-ester with 1-(butyloxycarbonyl)-3-(methylthio)propyl carbamic acid Rapamycin 42-ester with 1-((4-chlorophenyl)methoxycarbonyl)-2-(phenylmethylthio)ethyl carbamic acid Rapamycin 42-ester with 1-methoxycarbonyl-1-(trifluoromethyl)methyl carbamic acid Rapamycin 42-ester with 1-(2-methylpropoxycarbonyl)-2-chloroethyl carbamic acid Rapamycin 42-ester with 1-ethoxycarbonyl-3-(aminocarbonyl)propyl carbamic acid Rapamycin 42-ester with 1-methoxycarbonyl-2-(P-(2,3-dihydroxypropyloxy) phosphonoxy)ethyl carbamic acid Rapamycin 42-ester with 1-cyano-1-(ethoxycarbonyl)methyl carbamic acid Rapamycin 42-ester with 1-methoxycarbonyl-2-(carboxymethylthio)ethyl carbamic acid Rapamycin 42-ester with 1-phenoxycarbonyl-1-(2-thenyl)methyl carbamic acid Rapamycin 42-ester with 1-phenylmethoxycarbonyl-2-(sulfo)ethyl carbamic acid Rapamycin 42-ester with 4-(ethylthio)butylamine Rapamycin 42-ester with 2-phenylthioethyl carbamic acid Rapamycin 42-ester with 2-sulfothioethyl carbamic acid Rapamycin 42-ester with 2-thioethyl carbamic acid Rapamycin 42-ester with 2-benzoylthioethyl carbamic acid Rapamycin 42-ester with 2-phosphonothioethyl carbamic acid Rapamycin 42-ester with 2-(methylthio)propyl carbamic acid Rapamycin 42-ester with 1-ethoxycarbonyl-2-sulfinoethyl carbamic acid Rapamycin 42-ester with 2-(2-chloro-6-fluorophenylmethylthio)ethyl carbamic acid Rapamycin 42-ester with N-(2-imidazolyl)amino carbamic acid Rapamycin 42-ester with 2-(N,N-dipropylamino)ethyl carbamic acid Rapamycin 42-ester with 2-(N,N-bis-(2-hydroxyethyl)amino)ethyl carbamic acid Rapamycin 42-ester with 2-(N-phenylmethyl-N-((3-ethyl-5-methyl)-4-isoxazolylmethyl)ethyl carbamic acid Rapamycin 42-ester with 1-((N-methyl-N-carboxymethyl)amino)carbonylmethyl carbamic acid Rapamycin 42-ester with cyanomethyl carbamic acid Rapamycin 42-ester with 1-phenyl-1-cyanomethyl carbamic acid Rapamycin 42-ester with 1-chloro-1-(phenylsulfonyl)methyl carbamic acid Rapamycin 42-ester with 1-isoquinolyl carbamic acid Rapamycin 42-ester with 1-(4-chlorophenyl)-1-(2-(1,2,3,4-tetrahydroisoquinolyl))methyl carbamic acid

EXAMPLE 3

Rapamycin 42-ester with 2-(dimethylamino)ethyl carbamic acid

A solution of 100 mg rapamycin 42-p-nitrophenyl carbonate in 2 mL dichloromethane was treated at 0° C. under a nitrogen atmosphere with 44 mg N,N-dimethylethylenediamine in 0.5 mL dichloromethane. The reaction mixture was stirred at 0° C. under nitrogen for 0.5 hour. The reaction mixture was diluted with dichloromethane, washed with water, and dried over MgSO$_4$. After filtration, the dichloromethane solution was cooled to 0° C. under a nitrogen atmosphere and treated with 1.5 ml of 0.1N HCl solution in ether. The crystalline material was collected by filtration, washed with ether and dried at 56° under vacuum to afford 80 mg of the title compound as a white solid which was isolated as the hydrochloride dihydrate, mp 125°–130° (decomposition).

IR(KBr): 3400 (OH and NH), 1720 (lactone and ketone C=O), 1640 (amide C=O), 1450, 1240, 1090, and 980 cm$^{-1}$. NMR (DMSO-D$_6$, 400 MHz) δ7.36 (1H, —OC(O)NH), 3.34 (m, 2H, —NHCH$_2$), 3.10 (m, 2H, CH$_2$—N$^+$H(CH$_3$)$_2$), 3.26, 3.14, 3.04 (all s, 3H, —OCH$_3$), 2.76 (s, 6H—N$^+$H(CH$_3$)$_2$) ppm. MS (neg. ion FAB): 1027 (M$^-$), 590, 435, 167. Analysis Calcd. for C$_{56}$H$_{89}$N$_3$O$_{14}$.HCl.2 H$_2$O; C,61.09; H,8.60; N,3.81. Found: C,61.06; H,8.55; N,3.91.

EXAMPLE 4

Rapamycin 42-ester with aminocarbamic acid

A solution of 108 mg rapamycin 42-p-nitrophenyl carbonate in 5 mL dichloromethane, cooled to $-10°$ C. under a nitrogen atmosphere, was treated with 6.4 mg hydrazine in 0.4 mL dichloromethane. The reaction mixture was stirred at $-10°$ C. under nitrogen for five hours. The yellow suspension was filtered, the filtrate evaporated, and the yellow residue was chromatographed on silica gel. Elution with ethyl acetate/n-hexane (4/1) afforded 52 mg of the title compound as a white solid, mp 110°–115°.

IR(KBr): 3400 (OH and NH), 1720 (lactone and ketone C=O)), 1640 (amide C=O), 1450, 1090 and 750 cm$^{-1}$. $^1$H NMR (CDCl$_3$, 400 MHz): δ3.37, 3.34, 3.14 (all s, 3H, —OCH3) ppm. MS (neg ion FAB): 971 (M$^-$), 590,167.

EXAMPLE 5

Rapamycin 42-ester with hydroxycarbamic acid

A solution of 210 mg hydroxylamine hydrochloride in 3 ml 1N KOH aqueous solution was diluted with 3 mL tetrahydrofuran. The solution was stirred at $-78°$ C. under nitrogen and 110 mg of rapamycin 42-p-nitrophenyl carbonate was added. The resulting mixture was stirred at 0° C. under nitrogen for 3 hours, diluted with water, and extracted with ethyl acetate. The extract was washed with brine, dried with MgSO$_4$, and evaporated. The residue was chromatographed on silica gel. Elution with ethyl acetate/n-hexane (2/1.) afforded 20 mg of the title compound as a foam, mp 107°–110°.

IR(KBr): 3400 (OH and NH), 1740 (lactone C=O), 1720 (ketone C=O), 1640 (amide C=O), 1450, 1100, 985, 750 cm$^{-1}$. $^1$H NMR (CDCl$_3$, 400 MHz): δ3.37, 3.35, 3.14 (all s, 3H, —OCH$_3$) ppm. MS (neg ion FAB): 972 (M$^-$), 913,950.

EXAMPLE 6

Rapamycin 42-ester with 2-(pyridin-2-yl)-ethyl carbamic acid

A solution of 210 mg rapamycin 42-p-nitrophenyl carbonate in 8 ml dichloromethane was treated at $-10°$ under N$_2$ with 122 mg 2-(2-amino-ethyl)-pyridine in 1 ml dichloromethane. The reaction mixture was stirred at 0° under N$_2$ for one hour, diluted with 200 ml dichloromethane, washed with ice-cold 1N HCl , water, and dried with MgSO$_4$. The solvent was evaporated and the residue chromatographed on silica gel. Elution with ethyl acetate/n-hexane (4/1) afforded 70 mg of the title product as a white solid, mp 95°–98°.

IR (KBr): 3400 (OH and NH), 1720 (lactone and ketone C=O), 1645 (amide C=O), 1450, 1250, 1090, 1100 and 990 cm$^{-1}$. $^1$H NMR (CDCl$_3$, 400 MHz): δ8.52 (d, J=12 cps, 1H, proton c), 7.59 (t, 1H, proton b), 7.12 (m, 2H, protons a), 3.32, 3.31 and 3.12 (each s, 3H, OCH$_3$), 3.58 (t, 2H, protons e), 2.97 (t, 2H, protons d) ppm. MS (neg. ion FAB): 1061 (M$^-$), 590, 469.

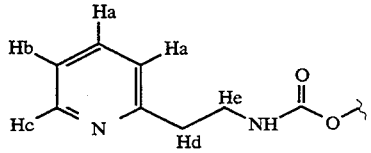

EXAMPLE 7

Rapamycin 42-ester with 2-(pyridin-2-yl)-ethyl carbamic acid hydrochloride salt

A solution of 330 mg rapamycin 42 ester with 2-(pyridin-2-yl)-ethyl carbamic acid in a mixture of one ml ethyl acetate and 4 ml ether was treated at −78° under N$_2$ with 0.5 ml 1N HCl (gas) in ether. The hydrochloride salt formed instantly. Stirring was continued at −78° under N$_2$ for ¼ hour. The product was collected by filtration, washed with ether, and dried in vacuum to afford 198 mg of the title product as a white solid, mp 102°–110° (dec).

IR (KBr): 3400 (OH, NH), 1720 (lactone and ketone C=O), 1640 (amide C=O), 1520, 1450, 1150, 1100, 990 cm$^{-1}$. $^1$H NMR (DMSO-D$_6$, 400 MHz): δ8.77 (d, J=12 cps, 1H, proton c), 8.40 (t, 1H, proton b), 7.83 (m, 2H, protons a), 3.63 (t, 2H, protons e), 3.00 (t, 2H, protons d), 3.43, 3.29, 3.03 (each s, 3H, —OCH$_3$) ppm. MS (neg ion FAB): 1061 (M$^-$), 590, 469.

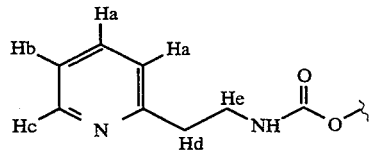

EXAMPLE 8

Rapamycin 42-ester with 2-(pyridin-2-yl)ethylcarbamic acid methanesulfonate salt A solution of 16 mg (0.16 mmole) methanesulfonic acid in 1 mL ether was added to a solution of 160 mg (0.15 mmole) rapamycin 42-ester with 2-(pyridin-2-yl)ethylcarbamic acid in 2 mL ethyl acetate and 4 mL ether at −78° C. under nitrogen. After warming to 20°, the solvent was decanted and the residue was triturated thrice with ether, leaving 108 mg title compound as a pale yellow solid, mp 95°–110° C. (dec).

IR (KBr): 3520, 2950, 1725, 1650, 1460, and 778 cm$^{-1}$. $^1$H NMR (CDCl3, 400 MHz): δ8.74 (d, 1H, 6-pyridyl); 3.35 (s, 3H, OMe); 3.34 (s, 3H, OMe); 3.14 (s, 3H, OMe); 2.92 (s, 3H, methanesulfonate) ppm. MS (neg ion FAB): 1061 (M−), 590.

EXAMPLE 9

Rapamycin 42-ester with 2-(pyridin-2-yl)ethylcarbamic acid maleate salt

A solution of 21 mg (0.18 mmole) maleic acid in 1.0 mL ether was added to a solution of 185 mg (0.17 mmole) rapamycin 42-ester with 2-(pyridin-2-yl)ethylcarbamic acid in 3 mL ethyl acetate and 2 mL ether at −78° C. under nitrogen. After warming to 15°, the mixture was diluted with ether, the solvent was decanted and the residue was triturated with ether. Filtration, followed by diluting the filtrate with hexane and refiltration yielded the title compound as a white solid, mp 101°–117° C.

IR (KBr): 3430, 2950, 1725, 1645, 1460, and 870 cm$^{-1}$. $^1$H NMR (CDCl$_3$, 400 MHz): δ8.76 (d, 1H, 6-pyridyl); 6.40 (s, 2H, maleic acid vinyl); 3.35 (s, 3H, OMe); 3.34 (s, 3H, OMe); 3.15 (s, 3H, OMe) ppm. MS (neg ion FAB): 1061 (M−), 590.

EXAMPLE 10

Rapamycin 42-ester with 2-pyridinylmethyl carbamic acid

A solution of 1.05 g rapamycin 42p-nitrophenyl carbonate in 20 ml dichloromethane was treated at −10° under N$_2$ with 620 mg 2-aminomethylpyridine in 1 ml dicholormethane. The reaction mixture was stirred at 0° under N$_2$ for 3 hours, diluted with 180 ml dichloromethane, washed with saturated NaHCO$_3$ (3×30 ml) and dried with MgSO$_4$. The solvent was evaporated and the residue chromatographed on silica gel. Elution with ethyl acetate/n-hexane (4/1) afforded 560 mg of the title product as a white solid, mp 94°–97°.

IR(KBr): 3420 (OH, NH), 1720 (lactone and ketone C=O), 1645 (amide C=O), 1520, 1450, 1250, 1100, 990 cm$^{-1}$. $^1$H NMR (CDCl$_3$, 400 MHz): δ8.53 (d, J=12 cps, 1H, proton d), 7.65 (m, 1H, proton c), 7.27 (d, J=12 cps, 1H, proton a), 7.17 (m, 1H, proton b), 5.72 (m, 1H, —NH), 4.49 (d, J=10 cps, 2H, protons e), 3.37, 3.32, 3.13 (each s, 3H, —OCH$_3$) ppm. MS (neg. ion FAB): 1047 (M$^-$), 590, 455.

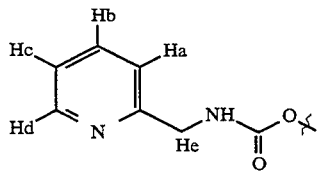

EXAMPLE 11

Rapamycin 42-ester with 2-pyridinylmethyl carbamic acid hydrohloride salt

A solution of 305 mg rapamycin 42-ester with 2-pyridinylmethyl carbamic acid in a mixture of one ml ethyl acetate and 4 ml ether was treated at −78° under N$_2$ with 0.55 ml 1N HCl solution. Crystalline material formed immediately. The reaction mixture was stirred at −78° under N$_2$ for ½ hrs, the solid material was collected by filtration, washed with ether and dried in vacuo to give 270 mg of the title product as a white solid, mp 109°–113° (dec).

IR (KBr): 3430 (OH, NH), 1740 (lactone, ketone C=O), 1645 (amide C=O), 1520, 1455, 1250, 1100, 995 cm$^{-1}$. $^1$H NMR (DMSO-D$_6$): δ8.70 (d, J=12 cps, 1H, proton d), 8.28 (t, 1H, proton c), 7.91 (t, 1H, proton b), 7.69 (t, 1H, proton b), 7.65 (d, 1H, proton a), 4.39 (d, 2H, protons e), 3.28, 3.14, 3.05 (each s, 3H, —OCH$_3$) ppm. MS (neg ion FAB): 1061 (M−), 590, 469.

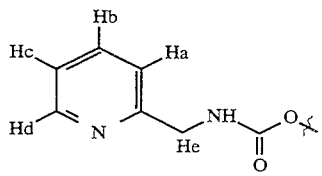

EXAMPLE 12

Rapamycin 42-ester with 3-pyridinylmethyl carbamic acid

The title compound was prepared according to the procedure in Example 6.

mp 109°–111° IR (KBr): 3400 (OH, NH), 1720 (lactone, ketone C=O), 1645 (amide C=O), 1450, 1250, 1100, 990 cm⁻¹. ¹H NMR (CDCl₃, 400 MHz): δ8.53 (m, 2H, proton c), 7.65 (m, 1H, proton b), 7.26 (m, 1H, proton a), 4.39 (d, J=12 cps, 2H, protons e), 3.36 (m), 3.32 (s), 3.12 (s) (all 3H,—OCH₃) ppm. MS (neg ion FAB): 1047 (M−), 590.

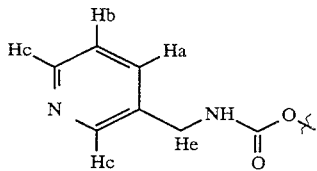

EXAMPLE 13

Rapamycin 42-ester with 3-pyridinylmethyl carbamic acid hydrochloride salt

The title compound was prepared according to the procedure in Example 7.

mp 106°–110° (dec) IR (KBr): 3400 (OH, NH), 1720 (lactone, ketone C=O), 1645 (amide C=O), 1460, 1250, 1110, 990 cm⁻¹. ¹H NMR (DMSO-D₆, 400 MHz): δ8.71 (m, 2H, protons c), 8.25 (d, J=12 cps, 1H, proton a), 7.91 (m, 1H, proton b), 4.34 (d, 2H, protons e), 3.26, 3.14, 3.04 (each s, 3H, —OCH₃) ppm. MS (neg ion FAB): 1047 (M−), 590.

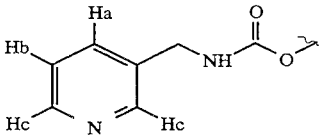

EXAMPLE 14

Rapamycin 42-ester with 4-pyridinylmethyl carbamic acid

The title compound was prepared according to the procedure in Example 6.

mp 109°–113° IR (KBr): 3400 (OH, NH), 1720 (lactone, ketone C=O), 1645 (amide C=O), 1520, 1450, 1250, 1100, 990 cm⁻¹. ¹H NMR (CDCl₃, 400 MHz): δ8.56 (d, J=12 cps, 2H, protons b), 7.24 (d, J=12 cps, 2H, protons a), 4.40 (d, J=13 cps, 2H, protons c), 3.38, 3.33, 3.14 (each s, 3H, —OCH₃) ppm. MS (neg ion FAB): 1047 (M−) 590.

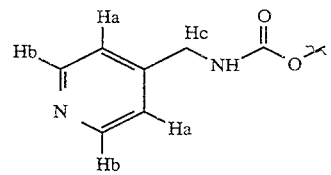

EXAMPLE 15

Rapamycin 42-ester with 4-pyridinylmethyl carbamic acid hydrochloride salt

The title compound was prepared according to the procedure in Example 7.

mp 109°–114° IR (KBr): 3400 (OH, NH), 1720 (lactone, ketone C=O), 1645 (amide C=O), 1510, 1455, 1250, 1100, 990 cm⁻¹. ¹H NMR (DMSO-D₆): δ8.81 (d, J=13 cps, 2H, protons b), 7.81 (d, J=13 cps, 2H, protons a), 4.43 (d, J=12 cps, 2H, protons e), 3.30, 3.14, 3.04 (each s, 3H, —OCH₃) ppm. MS (neg ion FAB): 1047 (M−), 590.

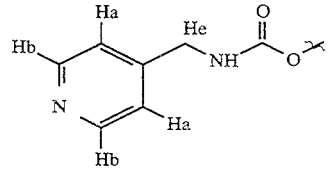

EXAMPLE 16

Rapamycin 42-ester with 2-furylmethyl carbamic acid

The title compound was prepared according to the procedure in Example 6.

mp 103°–105° IR (KBr): 3400 (OH, NH), 1720 (lactone, ketone C=O), 1645 (amide C=O), 1520, 1460, 1250, 1100, 990 cm⁻¹. ¹H NMR (CDCl₃, 400 MHz): δ7.35 (d, 1H, proton b), 6.32 (m, 1H, proton a), 6.24 (d, 1H, proton c), 4.36 (d, J=13 cps, 2H, protons e), 3.36, 3.33, 3.14 (each s, 3H, —OCH₃) ppm. MS (neg. ion FAB): 1036 (M−), 590.

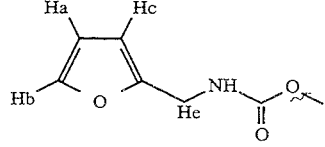

EXAMPLE 17

Rapamycin 42-ester with 2-pyridinylmethyl carbamic acid methanesulfonate salt

The title compound was prepared from the compound of Example 10 and methane sulfonic acid, and was isolated as a trihydrate.

mp 92°–95° IR(KBr): 3400 (OH, NH), 1720 (lactone, ketone C=O), 1640 (amide C=O), 1520, 1450, 1450, 1240–1160 (sulfonate), 1100, 1040 (sulfonate), 990 cm⁻¹. ¹H NMR (DMSO-D₆): δ8.72 (d, J=13 cps, 1H, proton e), 8.31 (t, 1H, proton c), 7.93 (t, 1H, —NH), 7.73 (t, 1H, proton b), 7.69 (d, J=15 cps, 1H, proton a), 4.44 (d, J=10) cps, 2H, protons f), 3.29 3.14, 3.04 (each s, 3H,—OCH₃),

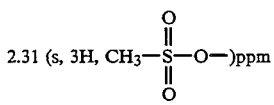

2.31 (s, 3H, CH$_3$—S(=O)$_2$—O—)ppm

C/H/N analysis for C$_{59}$H$_{29}$N$_3$O$_{17}$S$_1$.3 H$_2$O Calc 59.12/7.99/3.50 Found 59.48/7.95/3.41

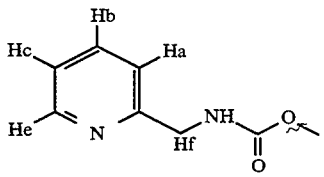

EXAMPLE 18

Rapamycin 42-ester with 4-hydroxybutyl carbamic acid

A solution of 600 mg rapamycin 42-p-nitrophenyl carbonate in 7.5 ml dichloromethane was treated at 0° under N$_2$ with 300 mg 4-amino-butanol in 0.5 ml dichloromethane. The yellow solution was stirred at 0° under N$_2$ for 2 hours. The mixture was diluted with 120 ml dicholoromethane, washed with 1N HCl, water, and dried with MgSO$_4$. The solvent was evaporated and the residue chromatographed on silica gel. Elution with ethyl acetate/n-hexane (2/1) afforded 245 mg of the title product as a solid, mp 105°–108°.

IR (KBr): 3420 (OH and NH), 1720 (lactone and ketone C=O), 1650 (amide C=O), 1530, 1455, 1250, 1110 and 990 cm$^{-1}$. $^1$H NMR (CDCl$_3$, 400 MHz): δ3.65 (t, 2H, —CH$_2$OH), 3.2 (m, 2H, —NHCH$_2$—), 3.37, 3.33 and 3.14 (all s, 3H each, —OCH$_3$) ppm. MS (neg ion FAB): 1028 (M−), 996, 590, 436, 167.

EXAMPLE 19

Rapamycin 42-ester with (S)-1-methyl-2-hydroxyethyl carbamic acid

A solution of 600 mg rapamycin 42-p-nitrophenyl carbonate in 7.5 ml dichloromethane was treated at 0° under N$_2$ with 500 mg (S)-(+)-2-amino-1-propanol in 0.5 ml dichloromethane. The yellow solution was stirred at 0° under N$_2$ for 2 hours. The mixture was diluted with 200 ml dichloromethane, washed with 1N HCl, water, and dried with MgSO$_4$. The solvent was evaporated and the residue chromatographed on silica gel. Elution with ethyl acetate/n-hexane (3/1) afforded 156 mg of the title product as a white solid, mp 99°–103°.

IR (KBr): 3440 (OH and NH), 1720 (lactone and ketone C=O), 1650 (amide C=O), 1520, 1455, 1110 and 995 cm$^{-1}$. $^1$H NMR (CDCl$_3$, 400 MHz): 3.70 (m, 2H, —CH$_2$OH), 3.38, 3.20, and 3.16 (all s, 3H each, —OCH$_3$), 1.15

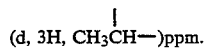

(d, 3H, CH$_3$CH—)ppm.
MS (ng.ion FAB): 1014 (M−), 983, 590 422, 167.

EXAMPLE 20

Rapamycin 42-ester with (R)-1-methyl-2-hydroxyethyl carbamic acid

A solution of 600 mg rapamycin 42-p-nitrophenyl carbonate in 7.5 ml dichloromethane was treated at 0° under N$_2$ with 600 mg (R)-(−)-2-amino-1-propanol in 0.5 ml dichloromethane. The yellow solution was stirred at 0° under N$_2$ for 2 hours. The mixture was diluted with 200 ml dichloromethane, washed with a saturated NaHCO$_3$ aqueous solution, 1N HCl solution, and dried with MgSO$_4$. The solvent was evaporated and the residue chromatographed on silica gel. Elution with ethyl acetate/n-hexane (3/1) afforded 260 mg of the title product as a white solid, mp 102–106°.

IR (KBr): 3440 (OH and NH), 1720 (lactone and ketone C=O), 1650 (amide C=O), 1520, 1460, 1110 and 1000 cm$^{-1}$. $^1$H NMR (CDCl$_3$, 400 MHz): δ3.70 (m, 2H, —CH$_2$OH), 3.37, 3.33 and 3.14 (all s, 3H, —OCH$_3$), 1.17

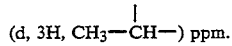

(d, 3H, CH$_3$—CH—) ppm.
MS (neg. ion FAB): 1014 (M−), 893, 590.

EXAMPLE 21

Rapamycin 42-ester with 2-(2-aminoethoxy)ethyl carbamic acid

A solution of 600 mg rapamycin 42-p-nitrophenyl carbonate in 7.5 ml dichloromethane was treated at 0° under N$_2$ with 500 mg 2-(2-aminoethoxy)ethanol in 0.5 ml dichloromethane. The yellow solution was stirred at 0° under N$_2$ for 1.5 hours. The mixture was diluted with 150 ml dichloromethane, washed with a saturated NaHCO$_3$ aqueous solution, 1N HCl solution, and dried with MgSO$_4$. The solvent was evaporated and the residue chromatographed on silica gel. Elution with ethyl acetate/n-hexane (3/1) afforded 265 mg of the title product as a white solid, mp 100°–102°.

IR(KBr): 3430 (OH and NH), 1720 (lactone and ketone C=O), 1650, 1520, 1455, 1110, 1020 and 990 cm$^{-1}$. $^1$H NMR (CDCl$_3$, 400 MHz): δ3.74 (t, 2H,—CH$_2$OH), 3.58 (m, 6H, —CH$_2$OCH$_2$CH$_2$—O—), 3.38, 3.33 and 3.14 (all s, 3H each, —OCH$_3$) ppm. MS (neg ion FAB): 1044 (M−), 590, 452, 167.

EXAMPLE 22

Rapamycin 42-ester with 4-(2-hydroxyethyl)piperazine-1-carboxylic acid

A solution of 1-(2-hydroxyethyl)piperazine) (130 mg, 1.0 mmole) in 1 mL dry dichloromethane was added to a solution of 330 mg rapamycin 42-p-nitrophenyl)carbonate (0.31 mmole) in 6 mL dry dichloromethane at −8° under nitrogen and stirred at −8° for 1.5 hours. The reaction mixture was partitioned between dichloromethane and water/brine, the aqueous portion was extracted with dichloromethane, the combined organic portion was washed with brine, dried over MgSO$_4$ and evaporated to a white solid foam. Flash chromatography through silica gel using 2% methanol in dichloromethane yielded 140 mg of the title compound as a white solid, mp 112°–120° C.

IR (KBr): 3450, 2950, 1725, 1650, 1460, 1250 and 995 cm$^{-1}$. NMR (CDCl$_3$, 400 MHz): δ3.64 (t (J=5.2Hz), 2H, H$_d$); 3.51 (broad, 4H, H$_a$); 3.39 (s, 3H, OMe); 3.33 (s, 3H, OMe); 3.14 (s, 3H, OMe); 2.57 (t (J=5.2 Hz), 2H, H$_c$); 2.49 (broad, 4H, H$_b$) ppm. MS (neg. ion FAB): m/z at 1069 (m−), 590.

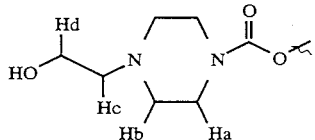

EXAMPLE 23

Rapamycin 42-ester with 4-(3-hydroxypropyl)piperazine-1-carboxylic acid

A solution of 130 mg (0.90 mmole) of 1-(3-hydroxypropyl)piperazine in 2 mL dichloromethane was added to a solution of 320 mg (0.30 mmole) rapamycin-42-(4nitrophenyl)carbonate in 6 mL dichloromethane under nitrogen at −5° C. and allowed to warm to 20° with stirring. After 4 hours, the reaction mixture was partitioned between dichloromethane and water/brine. The organic portion was washed with brine and flash chromatographed through silica gel using methanol (2.0 to 3.0%) in dichloromethane, yielding 115 mg product as a white solid, mp 104°-113° C.

IR (KBr): 3430, 2930, 1715, 1640,1450, 1240, and 985 cm$^{-1}$. NMR (CDCl3, 400 MHz): δ3.81 (t (J=5.2 Hz), 2H, Hd); 3.49 (broad, 4H, Ha); 3.38 (s, 3H, OMe); 3.33 (s, 3H, OMe); 3.13 (s, 3H, OMe); 2.62 (t (J=5.4 Hz), 2H, Hc); 2.48 (broad, 4H, Hb) ppm. MS (neg ion FAB): 1083 (M−), 590.

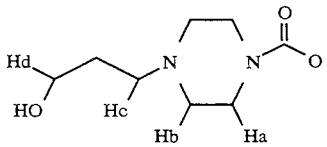

EXAMPLE 24

Rapamycin 42-ester with [3-[bis(2-hydroxyethyl)aminol propyl]carbamic acid

A solution of 130 mg (0.80 mmole) of N-(3-aminopropyl)diethanolamine in 2 mL dichloromethane was added to a solution of 330 mg (0.31 mmole) rapamycin-42-( 4-nitrophenyl)carbonate in 8 mL dichloromethane under nitrogen at 0° C. and stirred at that temperature for one hour. The reaction mixture was partitioned between dichloromethane and brine. The organic portion was washed with brine and flash chromatographed through silica gel using 5% methanol in dichloromethane to yield 150 mg product as a white solid, mp 93°-107° C. IR (KBr): 3420, 2935, 1715, 1640, 1450 and 985 cm$^{-1}$. NMR (CDCl3, 400MHz): δ5.69 (broad, 1H, Hj); 3.67 (mult, 6H, He and Hh); 3.36 (s, 3H, OMe); 3.33(s, 3H, OMe); 3.14 (s, 3H, OMe); 2.68 (mull, 6H, Hf and Hg) ppm. MS (neg ion FAB): 1101 (M−), 590.

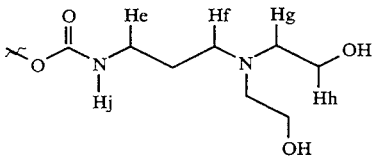

EXAMPLE 25

Rapamycin 42-ester with dihydroxyispropyl carbamic acid

To a 600 mg serinol in 3 ml methanol solution at −10° under N2, was added 250 mg rapamycin 42-p-nitrophenyl carbonate in 1 ml chloroform. The resulting solution was stirred at −10° under N2 for 2 hours, diluted with 120 ml chloroform, washed with water (3×20 ml), and dried with MgSO4. The solvent was evaporated and the residue chromatographed on silica gel. Elution with ethyl acetate/n-hexane (4/1) afforded 90 mg the title product as a solid, mp 108°-113°.

IR (KBr): 3450 (OH and NH), 1730 (ketone and lactone), 1655 (amide C=O), 1520, 1460, 1250, 1100, 1000 CM$^{-1}$. $^{1}$H NMR (CDCl3, 400 MHz): δ4.69 (m, 1H, C-42 proton), 3.75-3.84 (m, 4H, —CH2—) ppm. MS (neg. ion FAB): 1030 (M−), 590,438.

EXAMPLE 26

Rapamycin 42-ester with morpholine-4-carboxylic acid

A solution of 95 mg (1.1 mmole) morpholine in 1 mL dry dichloromethane was added to a stirred solution of 330 mg (0.31 mmole) rapamycin-42-(4nitrophenyl)carbonate in 6 mL dichloromethane at −5° C. under nitrogen; stirring was continued 4.5 hours at −5° and 2 hours at 20°. The reaction mixture was partitioned between dichloromethane and water/brine; the organic portion was washed with brine and flash chromatographed through silica gel using methanol (1.0 to 1.6%) in dichloromethane, yielding 70 mg product as a white solid, mp 105°-115° C.

IR (KBr): 3450, 2950, 1710, 1650, 1250, and 993 cm$^{-1}$. NMR (CDCl3, 400MHz): δ3.64 (4H, 3-morpholine); 3.46 (t (J=4.9 Hz), 4H, 2-morpholine); 3.37 (s, 3H, OMe); 3.32 (s, 3H, OMe); 3.12 (s, 3H, OMe) ppm. MS (neg ion FAB): 1026 (M−), 590.

EXAMPLE 27

Rapamycin 42-ester with 4-methylpiperazine-1-carboxylic acid

A solution of 95 mg (0.95 mmole) 1-methylpiperazine in 2 mL dichloromethane was added to a solution of 310 mg (0.29 mmole) rapamycin-42-(4-nitrophenyl)carbonate in 6 mL dichloromethane at 0° C. under nitrogen and stirred at 0° for 2 hours and at 20° for 2 hours. The reaction mixture was partitioned between dichloromethane and water/brine. The organic portion was washed with brine and flash chromatographed through silica gel using methanol (2.0 to 3.0%) in dichloromethane, yielding 120 mg product as a white solid, mp 108°-116° C.

IR (KBr): 3450, 2945, 1710, 1650, 1460, 1240, 1110, and 990cm$^{-1}$. NMR (CDCl3, 400 MHz): δ3.50 (broad, 4H, 2-piperazine); 3.39 (s, 3H, OMe); 3.33 (s, 3H, OMe); 3.14 (s, 3H, OMe); 2.36 (broad, 4H, 3-piperazine); 2.30 (s, 3H, NMe) ppm. MS (neg ion FAB): 1039 (M−), 590.

EXAMPLE 28

Rapamycin 42-ester with piperazine-1-carboxylic acid

A solution of 190 mg (2.2 mmole) piperazine in 4 mL dichloromethane was added to a solution of 550 mg (0.51 mmole) rapamycin-42-(4-nitrophenyl)carbonate in 12 mL dichloromethane at 0° C. under nitrogen and stirred 45 minutes. Partitioning between dichloromethane and water/brine, washing with brine and flash chromatography through silica gel using 5% methanol in dichloromethane yielded 350 mg product as a pale yellow solid, mp 120°-131° C.

IR (KBr): 3460, 2950, 1705, 1650, 1460, 1245, and 990 cm$^{-1}$. NMR (CDCl3, 400 MHz): δ4.8 (broad, 1H, NH); 3.46 (broad, 4H, 2piperazine); 3.39 (s, 3H, OMe); 3.33 (s, 3H, OMe); 3.14 (s, 3H, OMe); 2.83 (broad, 4H, 3piperazine); ppm.
MS (neg ion FAB): 1025 (M−), 590.

EXAMPLE 29

Rapamycin 42-ester with (toluene-4-sulfonylamino)-carbamic acid

A solution of 300 mg rapamycin 42-ester with aminocarbamic acid in 3 ml pyridine was treated at −10° C. under nitrogen atmosphere with 190 mg p-toluenesulfonyl chloride. The mixture was stirred at −10° C. for 10 minutes and stood at −14° C. for 18 hours. The pyridine was evaporated at room temperature under reduced pressure. The residue was dissolved in 200 ml dichloromethane, washed with water, dried with MgSO4 and evaporated. The crude product was chromatographed on silica gel. Elution with 2% methanol in dichloromethane afforded 115 mg of the title compound as a pale yellow solid, mp 128°-130° C.

IR (KBr): 3440 (OH, NH), 1720 (lactone and ketone C=O). 1645 (amide C=O), 1450, 1340 (—NHSO2—), 1165 (—NH—SO2—), 1090 and 990 cm$^{-1}$. 1H—NMR (CDCl3, 400 MHz): δ7.79 (d, J=12 cps, 2H, proton a), 7.29 (d, J=12 cps, 2H, proton b), 3.31, 3.28, 3.12 (all S, 3H, three methoxys) 2.40 (S, 3H, aromatic methyl) ppm.

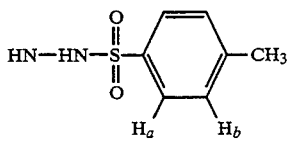

MS (neg. ion FAB): 1125.5(M−); 970.5, 590.3. UV (CHCl3): λ$_{max}$ 270 (ε34,367), 279 (ε43,160), 291 (ε33,160) mμ.

EXAMPLE 30

Rapamycin 42-ester with 2-benzoyl-hydrazine-carboxiylic acid

A solution of 240 mg rapamycin 42-ester with aminocarbamic acid in 3 ml pyridine was treated at −10° C. under nitrogen atmosphere with 100 mg benzoyl chloride. The mixture was stirred at room temperature for 5 hours and stood at −14° C. for 18 hours. The pyridine was evaporated at room temperature under reduced pressure. The residue was dissolved in 200 ml dichloromethane, washed with water, dried and evaporated. The crude product was chromatographed on silica gel. Elution with 3% methanol in dichloro-methane afforded 196 mg of the title compound as a white solid, mp 155°-160° C.

IR (KBr) 3400 (OH, NH), 1720 (lactone and ketone C=O), 1643 (amide C=O), 1450, 1243, 1095 and 990 cm$^{-1}$. 1HNMR (CDCl3, 400 MHz): δ7.80 (d, J=12 cps 2H, proton a), 7.51 (m, 1H, proton c). 7.43 (m, 2H, proton b). 3.37 (d, 3H, C-41 methoxys), 3.31, 3.12 (both s, 3H, the other two methoxys) ppm.

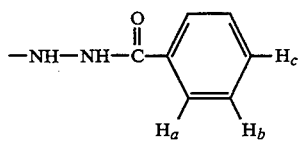

MS (neg. ion FAB): 1075.6 (M−), 590,161.

EXAMPLE 31

Rapamvcin 42-ester with 2-(pyridine-3-yl)hydrazinecarboxylic acid

A solution of 151 mg nicotinic acid in 4 ml N,N-dimethylformamide was treated at room temperature under N2 with 188 mg 1-hydroxybenzotriazole. The mixture was stirred for 10 minutes and 254 mg N,N-dicyclohexylcarbodiimide was added to the solution. After being stirred for additional 11/4 hours, the reaction mixture became a suspension, which was treated with 600 mg rapamycin 42-ester with aminocarbamic acid in 2 ml N,N-dimethylformamide. After stirring for additional 18 hours, the suspension was filtered and the filtrate was evaporated at room temperature under reduced pressure. The residue was dissolved in 200 ml dichloromethane, washed successively with cold 1N HCl, saturated sodium bicarbonate, and water, and then was dried. The dichloromethane was evaporated and the residue was chromatographed on silica gel. Elution with ethyl acetate/n-hexane (4/1) afforded 190 mg of the title product as a white solid, mp 109-113:

IR(KBr): 3440 (OH, NH), 1725 (lactone, ketone C=O), 1640 (amide C=O), 1455, 1250, 1200, 1090 and 990 cm$^{-1}$. 1HNMR (CDCl3, 400 MHz): δ9.03 (s, 1H, proton a), 8.75 (d, J-12 cps, 1H, proton b), 8.13 (d, J=13 cps, 1H, proton d), 7.40 (m, 1H, proton c), 3.36 (d, 3H, C41-methoxy), 3.31, 3.12 (both S, 3H, the other two methoxys) ppm.

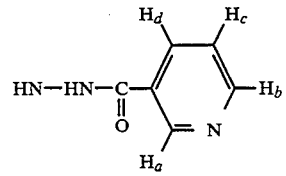

MS (neg. ion FAB): 1076.6 (M$^{31}$), 590.

EXAMPLE 32

Rapamycin 42-ester with 2-(pyridin-3-ylmethylene)hydrazine-carboxylic acid

A solution of 300 mg rapamycin 42-ester with aminocarbamic acid in 6 ml benzene was treated with 99.6 mg 3-pyridine carboxaldehyde, and refluxed through a Dean-Stark water sparator for 16 hours. The solvent was evaporated and the residue was chromatographed on silica gel. Elution with ethyl acetate/n-hexane =2/1 afforded 134 mg of the title product as a yellow solid, mp 128°-132°.

IR (KBr): 3450 (OH, NH), 1730 (lactone and, ketone C=O),

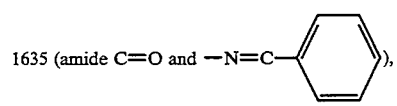

1455, 1210, 1100, 1040 and 990 cm$^{-1}$. 1HNMR (CDCl3, 400 MHz): δ8.68 (d, J=10 cps, 1H, proton a), 7.83 (m, 1H, proton b), 7.40 (d, J=12 cps, 1H, proton d), 7.32 (m, 1H, proton c), 3.41 (d, 3H, C41-methoxy), 3.32, 3.13 (both s, 3H, the other methoxys) ppm. MS (neg. ion FAB ): 1060 (M−). 590.

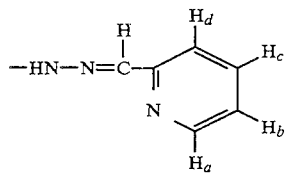

EXAMPLE 33

Rapamycin 42-ester with mycophenolyl-hydrazine-carboxylic acid

A solution of 395 mg mycophenolic acid in 6 ml N,N-dimethyl-formamide was treated at room temperature under $N_2$ with 188 mg 1-hydroxybenzotriazole. After stiring for 15 minutes, 254 mg N,N-dicyclohexylcarbodiimide was added to the solution. The mixture was stirred for one hour during which time the reaction mixture became a suspension, which was treated with 600 mg rapamycin 42-ester with aminocarbamic acid in 2.5 ml N,N-dimethylformamide. The mixture was stirred at room temperature for additional 20 hours, the suspension was filtered, and the filtrate was evaporated at room temperature under reduced pressure. The residue was dissolved in 220 ml dichloromethane, washed successively with cold 1N HCl, saturated sodium bicarbonate, water, and then dried. The dichloromethane solution was evaporated and the residue was chromatographed on silica gel. Elution with ethyl acetate/n-hexane (3/1) afforded 380 mg of the title product as a white solid, mp 110°–115° C.

IR (KBr): 3450 (OH, NH), 1730 (lactone, ketone C=O), 1635 (amide C=O), 1450, 1375, 1195, 1075 and 990 cm$^{-1}$. $^1$H-NMR (CDCl$_3$, 400 MHz): δ5.28 (m, 1H proton a), 5.20 (S. 2H, protons b), 4.57 (m, 1H, C-42 proton), 3.76 (s, 3H, aromatic methoxy), 3.37 (s, 3H, C-41 methoxy), 3.33, 3.13 (both s, 3H, the other methoxy), 2.15 (s, 3H, aromatic methyl) ppm. MS (neg. ion FAB): 1273.4 (m−), 661.06, 590.2.

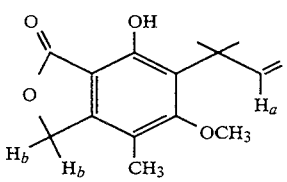

EXAMPLE 34

Rapamycin 42-ester with 1-piperidylcarbamic acid

A solution of 560 mg rapamycin 42-p-onitrophenyl carbonate in 6 ml dimethyl sulfoxide was treated at room temperature with 160 mg 1-aminopiperidine and stirred for five hours. The mixture was diluted with 120 ml dichloromethane, washed with water, dried and evaporated. The residue was chromatographed on silica gel. Elution with 2% methanol in dichloromethane afforded 145 mg of the title product as a white solid, mp 110°–113° C.

IR (KBr): 3420 (OH and NH), 1717 (lactone and ketone C=O), 1640 (amide C=O), 1460, 1230, 1100 and 990cm$^{-1}$. $^1$H-NMR (CDCl$_3$, 400 MHz): δ4.55 (m, 1H, C=42 proton), 3.39, 3.37 3.12 (each s, 3H, methoxys), 2.70 (m, 4H, protons b), 1.74 (m, 6H, protons a) ppm.

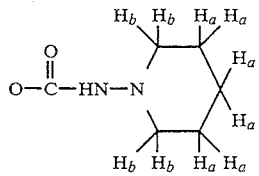

MS (neg. ion FAB): 1039.8(m−), 590.5, 447.4

EXAMPLE 35

Rapamycin 42-ester with 1-piperidylcarbamic acid hydrochloride salt

A stirred solution of 252 mg rapamycin 42-ester with 1-piperidylcarbamic acid in a mixture of 1 ml ethyl acetate and 4 ml ether was cooled to 0° C./N$_2$ and treated with 0.36 ml of 1M hydrogen chloride in ether. A white crystalline material was formed, which was stirred at O° C./N$_2$ for additional 10 minutes. The precipitate was collected, washed with ether and dried in vacuum to afford 130 mg of the title product as a white solid, mp 120°–125° C.

IR (KBr): 3400 (OH, NH), 1735 (lactone and ketone C=O), 1640 (amide C=O), 1450, 1370, 1240, 1100 and 990 cm$^{-1}$. $^1$H-NMR (DMSO-D$_6$, 400 MHz): δ4.92 (m, 1H, C-42 proton), 3.26, 3.15, 3.04 (each s, 3H, methoxys), 1.68 (m, 6H, protons a) ppm.

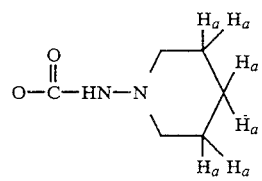

MS (neg. ion FAB): 1039.5 (M−), 590.3,447.3.

EXAMPLE 36

Rapamycin 42-ester with [4-(2-hydroxyethyl)-piperazyl]-1-aminocarboxylic acid

A solution of 1.20 g rapamycin 42-p-nitrophenyl carbonate in 8 ml N,N-dimethylformamide was treated at room temperature under N$_2$ with 320 mg 1-amino-4-(2-hydroxyethyl) piperazine and stirred for 6 hours. It was diluted with 160 ml ethylacetate, washed with water, dried and evaporated. The residue was chromatographed on silica gel. Elution with 4% methanol in dichloromethane afforded 150 mg of the title product as a white solid, mp 115°–120° C.

IR (KBr): 3440 (NH, OH), 1720 (lactone and ketone C=O), 1640 (amide C=O). 1455, 1250, 1085 and 990 cm$^{-1}$. $^1$H-NMR (CDCl$_3$, 400 MHz): δ4.57 (m, 1H, C-42 proton), 3.61 (t, 2H, protons d), 3.30, 3.28, 3.14 (all s, 3H, methoxys), 2.87 (m, 4H, protons c), 2.67 (m, 4H, protons b), 2.60 (t, 2H, protons a) ppm.

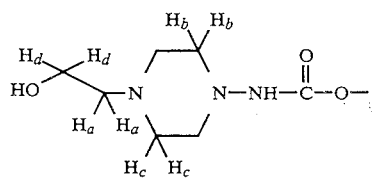

MS (neg. ion FAB): 1084.6 (M−), 590.3.

EXAMPLE 37

Rapamycin 42-ester with acetylaminocarbamic acid

A solution of 500 mg rapamycin 42-ester with aminocarbamic acid in 3 ml pyridine was treated at 0° C. under nitrogen with 306 mg acetic anhydride and stirred at 0° C./N$_2$ for two hours. The mixture was diluted with 70 ml ethyl acetate, washed with water, dried and evaporated. The residue was chromatographed on silica gel. Elution with 3% methanol in dichloromethane afforded 74 mg the title product as a white solid, mp 120°–125° C.

IR (KBr): 3420 (NH, OH), 1720 (lactone and ketone C=O), 1640 (amide C=O), 1450, 1255, 1100 and 990 cm$^{-1}$. $^1$HNMR (CDCl$_3$. 400 MHz): δ7.37, 6.65 (each m, 1H, —NH). 4.61 (m, 1H, C-41 proton), 3.39, 3.34, 3.14 (each s, 3H, methoxy),

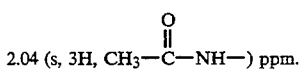

2.04 (s, 3H, CH$_3$—C—NH—) ppm.

MS (neg. ion FAB): 1013.7 (M$^-$). 590.5, 421.4.

EXAMPLE 38

Rapamycin 42-ester with 2-phenylhydrazinecarboxylic acid

To a solution of 0.5080 g (0.4706 mmol) of 42-O-(4-Nitrophenoxycarbonyl)rapamycin in 3 ml of DMF was added 0.046 ml (0.4674 mmol) of phenylhydrazine. The reaction mixture was allowed to stir under nitrogen at ambient temperature for 48 hours, then was diluted with ethyl acetate and washed with portions of H$_2$O and brine. The organic phase was dried over magnesium sulfate, filtered and concentrated under vacuum to yield crude product. Purification by flash column chromatography (elution with 50% then 60% ethyl acetate/hexanes) gave 0.0922 g (19%) of the title compound as a pale yellow solid.

$^1$H NMR (DMSO) δ8.99 and 7.61(N—H, 2H), 7.11 –6.62 (aromatic-H, 5H), 4.41(42C—H, 1H) MS (—) FAB m/z: 1047 (M$^-$), 590 (Southern Fragment), 455 (Northern Fragment).

EXAMPLE 39

Rapamycin 42-ester with 2-(phthalazin-2-yl)-hydrazine carboxylic acid

To 0.911 g (4.632 retool) of hydralazine hydrochloride was added one equivalent of 0.1M sodiumhydroxide/methanol after which the solvent was removed in vacuo. To the solution of the free base in 30 ml of DMF was added 5.003 g (4.635 mmol) of 42-O-(4-Nitrophenoxycarbonyl)rapamycin. The reaction mixture was allowed to stir under nitrogen at ambient temperature for 24 hours, then was diluted with ethyl acetate and washed with portions of H$_2$O and brine. The organic phase was dried over magnesium sulfate, filtered and concentrated under vacuum to yield crude product. Purification by flash column chromatography (elution with 80% ethyl acetate/hexanes then 100% ethyl acetate) gave 0.6665 g (13%) of the title compound as a pale yellow solid.

$^1$H NMR (DMSO) δ9.4 and 9.0 (NH, 2H), 7.81 (hetero-H, 2H), 7.82 –7.57 (aromatic—H, 4H), 4.48 (42C—H, 1H). MS (—) FAB m/z: 1099 (M$^-$), 590 (Southern Fragment), 475 (Northern Fragment).

EXAMPLE 40

Rapamycin 42-ester with 2-(quinolin-3-yl)-hydrazinecarboxylic acid

To 1.07 1 g (4.6155 mmol) of 3-hydrazinoquinoline dihydrochloride was added two equivalents of 0.1M sodium hydroxide/methanol after which the solvent was removed in vacuo. To a solution of the free base in 30 ml of DMF was added 5.002 g (4.634 retool) of 42-O-(4-Nitro-phenoxycarbonyl)rapamycin. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with ethyl acetate) gave 0.1133 g (2%) of the title compound as a pale yellow solid.

$^1$H NMR (DMSO) δ9.3 and 7.2 (NH, 2H), 8.5 and 8.32 (hetero-H, 2H), 7.85 –7.45 (aromatic—H, 4H), 4.48 (42C—H, 1H). MS (—) FAB m/z: 1098 (M$^-$), 590 (Southern Fragment), 506 (Northern Fragment).

EXAMPLE 41

Rapamycin 42-ester with 2-(6-methyl-pyridazin-3-yl)-hydrazinecarboxylic acid

To a solution of 5.0057 g (4.638 retool) of 42-O-(4-Nitrophenoxycarbonyl)rapamycin in 25 ml of DMF was added 0.5757 g (4.637 mmol) of 3-methylpyridazin-6-yl hydrazine. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 10% isopropanol/methylene chloride (2x)) gave 1.2905 g (26%) of the title compound as a pale yellow solid.

$^1$H NMR (DMSO) δ7.7–7.55 (hetero-H, 2H), 5.3 (NH, 2H), 4.5 (42C—H, 1H), 2.6 (CH$_3$, 3H). MS (—) FAB m/z: 1063 (M$^-$), 590 (Southern Fragment), 471 (Northern Fragment).

EXAMPLE 42

Rapamycin 42-ester with 2-(pyrazin-2-yl)-hydrazine carboxylic acid

To a solution of 5.0031 g (4.635 retool) of 42-O-(4—Nitro-phenoxycarbonyl)rapamycin in 20 ml of DMF was added 0.5104 g (4.635 mmol) of hydrazinopyrazine. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (3 successive columns were run eluting with 100% ethyl acetate/hexanes (2x) followed with 7.5% isopropanol/methylene chloride) gave 0.6064 g (12%) of the title compound as a white solid.

$^1$H NMR (DMSO) δ9.2 and 8.79 (N—H, 2H), 8.02–7.88 (hereto-H, 3H), 4.41 (42C—H, 1H). MS (—) FAB m/z: 1049 (M$^-$), 590 (Southern Fragment), 457 (Northern Fragment).

EXAMPLE 43

Rapamycin 42-ester with 2-(pyrimidin-2-yl)-hydrazinecarboxylic acid

To a solution of 5.0034 g (4.636 mmol) of 4-O-(4-Nitro-phenoxycarbonyl)rapamycin in 20 ml of DMF was added 0.5106 g (4.636 mmol) of 2-hydrazinopyrimidine. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 80% then 100% ethyl acetate/hexanes followed with a second column eluting with 7.5% isopropanol/methylene chloride) gave 0.700 g (14%) of the title compound as a white solid.

$^1$H NMR (DMSO) δ9.0 and 8.85 (N—H, 2H), 8.38 and 6.75 (hetero-H, 3H), 4.4 (42C—H, 1H). MS (−) FAB m/z: 1049 (M$^-$), 590 (Southern Fragment), 457 (Northern Fragment).

EXAMPLE 44

Rapamycin 42-ester with 2.2-dimethyl-hydrazinecarboxylic acid

To a solution of 0.5057 g (0.4685 mmol) of 42-O-(4-Nitrophenoxycarbonyl)rapamycin in 3 ml of DMF was added 0.035 ml (0.4685 mmol) of 1,1-dimethylhydrazine. The reaction mixture was allowed to stir under nitrogen at ambient temperature for 24 hours, then diluted with ethyl acetate and washed with portions of H$_2$O and brine. The organic phase was dried over magnesium sulfate, filtered and concentrated under vacuum to yield crude product. Purification by flash column chromatography (elution with 5% then 7% methanol/methylene chloride) gave 0.1062 g (22%) of the title compound as a pale yellow solid.

$^1$H NMR (DMSO) δ8.19 (N—H, 1H), 4.39 (42C—H, 1H), 2.4(dimethyl, 6H). MS (−) FAB m/z: 999 (M$^-$), 590 (Southern Fragment), 407 (Northern Fragment).

EXAMPLE 45

Rapamycin 42-ester with (4-methyl-piperazin-1-yl)-carbamic acid

To a solution of 1.0268 g (0.9513 mmol) of 42-O-(4-Nitrophenoxycarbonyl)rapamycin in 8 ml of DMF was added 0.115 ml (0.9555 retool) of 1-amino-4-methyl piperazine. The reaction mixture was allowed to stir under nitrogen for 24 hours at ambient temperature, then diluted with ethyl acetate and washed with portions of H$_2$O and brine. The organic phase was dried over magnesium sulfate, filtered and concentrated under vacuum to yield crude product. Purification by flash column chromatography (elution with 7% then 10% methanol/methylene chloride ) gave 0.447 g (44% ) of the title compound as a white solid. $^1$H NMR (DMSO) δ8.22 (N—H, 1H), 4.38 (42C—H, 1H), 2.7 and 2.4 (CH$_2$, 8H), 2.2 (CH$_3$, 3H). MS (−) FAB m/z: 1054 (M$^-$), 590 (Southern Fragment), 452 (Northern Fragment).

EXAMPLE 46

Rapamycin 42-ester with 2-(pyridin-2-yl)-hydrazinecarboxylic acid

To a solution of 1.009 g (0.9353 mmol) of 42-O-(4-Nitrophenoxycarbonyl)rapamycin in 5 ml of DMF was added 0.1021 g (0.9355 mmol) of 2hydrazinopyridine. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 80% ethyl acetate/hexanes followed by 7% methanol/methylene chloride) gave 0.1557 g (16%) of the title compound as a white solid.

$^1$H NMR (DMSO) δ9.0 and 8.2 (N—H, 2H), 8.0–6.6 (aromatic-H, 4H), 4.4 (42C—H, 1H). MS (−) FAB m/z: 1048 (M$^-$), 590 (Southern Fragment), 456 (Northern Fragment).

EXAMPLE 47

Rapamycin 42-ester with 2-(benzothiazol-2-yl)-hydrazinecarboxylic acid

To a solution of 1.005 g (0.9311 mmol) of 42-O-(4-Nitrophenoxycarbonyl)rapamycin in 6 ml of DMF was added 0.3076 g (1.8618 mmol) of 2-hydrazinobenzothiazole. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 80% then 100% ethyl acetate/hexanes) gave 0.4625 g (15%) of the title compound as a pale pink solid.

$^1$H NMR (DMSO) δ7.95 and 7.75 (N—H, 2H), 7.82 and 7.43 (aromatic-H, 4H), 4.65 (42C—H, 1H). MS (−) FAB m/z: 1104 (M$^-$), 590 (Southern Fragment).

EXAMPLE 48

Rapamycin 42-ester with 2-(quinoxalin-2-yl)-hydrazinecarboxylic acid

To a solution of 5.005 g (4.637 retool) of 42-O- (4-Nitrophenoxycarbonyl)rapamycin in 25 ml of DMF was added 0.7428 g (4.637 mmol) of quinoxaline-2-hydrazine. The reaction mixture was allowed to stir under nitrogen for 24 hours at ambient temperature, then was diluted with ethyl acetate and washed with portions of H$_2$O and brine. The organic phase was dried over magnesium sulfate, filtered and concentrated under vacuum to yield crude product. Purification by precipitation of product from ethylacetate containing one impurity followed with flash column chromatography (elution with 7.5% isopropanol/methylene chloride) gave 0.3897 g (7%) of the title compound as a beige solid.

$^1$H NMR (DMSO) δ9.38 and 7.85 (NH, 2H), 8.4 (hetero-H, 1H), 7.6 and 7.45 (aromatic-H, 4H), 4.45 (42C—H, 1H). MS (−) FAB m/z: 1099 (M$^-$), 590 (Southern Fragment), 475 (Northern Fragment).

EXAMPLE 49

Rapamycin 42-ester with (ethoxycarbonyl)-hydrazinecarboxylic acid

To a solution of 1.05 g (0.9728 retool) of 42-O-(4-Nitrophenoxycarbonyl)rapamycin in 8 ml of DMF was added 0.1013 g (0.9730 mmol) of ethylcarbazate. The reaction was allowed to stir under nitrogen for 60 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 60% then 80% ethyl acetate/hexanes) gave 0.1032 g (10%) of the title compound as a pale yellow solid.

1H NMR (DMSO) δ9.0 (N—H, 2H), 4.4 (42C—H, 1H), 4.0 (CH$_2$, 2H), 1.18 (CH$_3$, 3H). MS (−) FAB m/z:

1043 (M−), 590 (Southern Fragment), 451 (Northern Fragment).

EXAMPLE 50

Rapamycin 42-ester with 2-(4-sulfamoylphenyl)-hydrazinecarboxylic acid

To 0.51 g (2.3 retool) of 4-sulfonamidophenylhydrazine hydrochloride was added one equivalent of 0.1M sodium hydroxide/methanol after which the solvent was removed in vacuo. To a solution of the free base in 10 ml of DMF, was added 0.56 g (4.6 retool) 1-(3-dimethylaminopropyl)-3-ethylcarbodiimide hydrochloride and 2.5 g (2.3 mmol) of 42-O-(4-Nitro-phenoxycarbonyl)rapamycin. The reaction mixture was allowed to stir under nitrogen for 48 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 3%, 5%, and 10% isopropanol/methylenechloride) gave 0.240 g (9%) of the title compound as a pale yellow solid.

$^1$H NMR (DMSO) d 9.2 and 8.3 (NH, 2H), 7.6 and 6.9 (aromatic-H, 4H), 7.0 (sulphpnamido-H, 2H), 4.42 (42C—H, 1H).

What is claimed is:
1. A compound of the structure

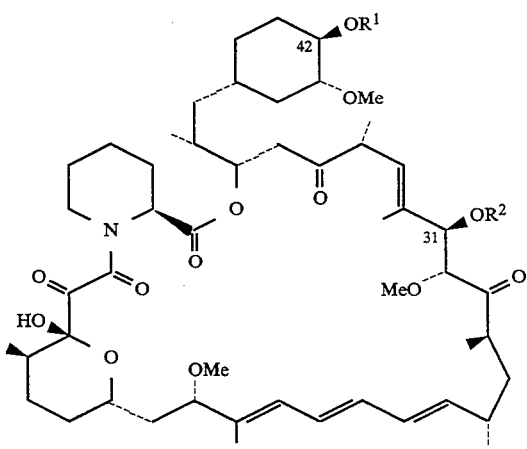

III wherein R$^1$ and R$^2$ are each, independently, hydrogen, —CONH—A—(CR$^5$R$^6$)$_n$—B, —CONR$^{11}$—A—(CR$^5$R$^6$)$_n$—B,

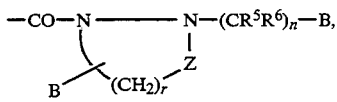

or —CONR$^7$—N⟨ ⟩;

R$^5$, R$^6$, and B are each, independently, hydrogen, alkyl of 1-6 carbon atoms, alkenyl of 2-7 carbon atoms, alkynyl of 2-7 carbon atoms, hydroxyalkyl of 1-6 carbon atoms, alkoxyalkyl of 2-12 carbon atoms, alkylthioalkyl of 2-12 carbon atoms, alkylaminoalkyl of 2-12 carbon atoms, dialkylaminoalkyl of 3-12 carbon atoms, arylalkyl of 7-10 carbon atoms, cycloalkyl of 3-8 carbon atoms, —OR$^7$, —SR$^7$, halogen, —CN, —NO$_2$, —CF$_3$, —COR$^7$, —CO$_2$R$^7$, —CONHR$^7$, —SO$_2$R$^7$, —OSO$_3$R$^7$, —NR$^7$R$^8$, —NHCOR$^7$, —NHSO$_2$R$^7$, —SO$_2$NR$^7$R$^8$, or Ar;

R$^7$ and R$^8$ are each, independently, hydrogen, alkyl of 1-6 carbon atoms, arylakyl of 7-10 carbon atoms, alkenyl of 2-7 carbon atoms, alkynyl of 2-7 carbon atoms, hydroyalkyl of 1-6 carbon atoms, alkoxyalkyl of 2-12 carbon atoms, alkylthioalkyl of 2-12 carbon atoms, alkylaminoalkyl of 2-12 carbon atoms, dialkylaminoalkyl of 3-12 carbon atoms, cycloalkyl of 3-8 carbon atoms, or Ar;

R$^{11}$ is alkyl of 1-6 carbon atoms, arylalkyl of 7-10 carbon atoms, alkenyl of 2-7 carbon atoms, alkynyl of 2-7 carbon atoms, hydroxyalkyl of 1-6 carbon atoms, alkoxyalkyl of 2-12 carbon atoms, alkylthioalkyl of 2-12 carbon atoms, alkylaminoalkyl of 2-12 carbon atoms, dialkylaminoalkyl of 3-12 carbon atoms, cycloalkyl of 3-8 carbon atoms, or Ar;

A is —NR$^7$—, —NHCO—, —N=C—, or —NHSO—;

Z is —CH$_2$— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3, -dihydroisobenzofuran-5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, alkylcarbonyl of 2-7 carbon atoms, carbamyl, alkylcarbamyl of 2-7 carbon atoms, dialkylcarbamyl of 3-13 carbon atoms, aminosulfonyl, alkylaminosulfonyl of 1-6 carbon atoms, dialkylaminosulfonyl of 2-12 carbon atoms, arylaminosulfonyl, alkylsulfonyl of 1-6 carbon atoms, arylsulfonyl, —SO$_3$H, and —CO$_2$H;

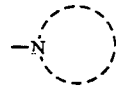

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1-6 carbon atoms, arylakyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1–6 carbon atoms per alkyl group, dialkylaminoalkyl of 3–12 carbon atoms, hydroyalkyl of 1–6 carbon atoms, alkoxyalkyl of 2–12 carbon atoms, alkylthio of 1–6 carbon atoms, —SO$_3$H, and —CO$_2$H;

n=0–6;

r=1–4;

with the proviso that R$^1$ and R$^2$ are not both hydrogen and further provided that when n=0, B is not —NR$^7$R$^8$, —NHCOR$^7$, —N=C—, or —NHSO$_2$R$^7$; or a pharmaceutically acceptable salt thereof.

2. The compound of claim 1 wherein R$^2$ is hydrogen or a pharmaceutically acceptable salt thereof.

3. The compound of claim 2 wherein R$^1$ is —CONH—A—(CR$^5$R$^6$)$_n$—B or a pharmaceutically acceptable salt thereof.

4. The compound of claim 3 wherein B is Ar or a pharmaceutically acceptable salt thereof.

5. The compound of claim 4 wherein n=0 or a pharmaceutically acceptable salt thereof.

6. The compound of claim 5 wherein A is —NR$^7$— or a pharmaceutically acceptable salt thereof.

7. The compound of claim 2 wherein R$^1$ is

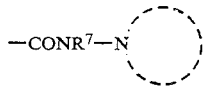

or a pharmaceutically acceptable salt thereof.

8. The compound according to claim 7 wherein R$^7$ is hydrogen and

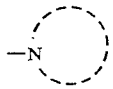

is piperidinyl or piperazinyl or a pharmaceutically acceptable salt thereof.

9. The compound of claim 1 which is rapamycin 42-ester with (toluene-4-sulfonylamino)-carbamic acid or a pharmaceutically acceptable salt thereof.

10. The compound of claim 1 which is rapamycin 42-ester with 2-benzoyl-hydrazine-carboxiylic acid or a pharmaceutically acceptable salt thereof.

11. The compound of claim 1 which is rapamycin 42-ester with 2-(pyridine-3-yl)hydrazine-carboxylic acid or a pharmaceutically acceptable salt thereof.

12. The compound of claim 1 which is rapamycin 42-ester with 2-(pyridin-3-ylmethylene)hydrazine-carboxylic acid or a pharmaceutically acceptable salt thereof.

13. The compound of claim 1 which is rapamycin 42-ester with mycophenolyl-hydrazine-carboxylic acid or a pharmaceutically acceptable salt thereof.

14. The compound of claim 1 which is rapamycin 42-ester with 1-piperidylcarbamic acid or a pharmaceutically acceptable salt thereof.

15. The compound of claim 1 which is rapamycin 42-ester with 1-piperidylcarbamic acid hydrochloride salt.

16. The compound of claim 1 which is rapamycin 42-ester with [4-(2-hydroxyethyl)-piperazyl]-1-aminocarboxylic acid or a pharmaceutically acceptable salt thereof.

17. The compound of claim 1 which is rapamycin 42-ester with acetylaminocarbamic acid or a pharmaceutically acceptable salt thereof.

18. The compound of claim 1 which rapamycin 42-ester with 2-phenyl-hydrazinecarboxylic acid is or a pharmaceutically acceptable salt thereof.

19. The compound of claim 1 which is rapamycin 42-ester with 2-(phthalazin-2-yl)-hydrazine carboxylic acid or a pharmaceutically acceptable salt thereof.

20. The compound of claim 1 which is rapamycin 42-ester with 2-(quinolin-3-yl)-hydrazinecarboxylic acid or a pharmaceutically acceptable salt thereof.

21. The compound of claim 1 which is rapamycin 42-ester with 2-(6-methyl-pyridazin-3-yl)-hydrazinecarboxylic acid or a pharmaceutically acceptable salt thereof.

22. The compound of claim 1 which is rapamycin 42-ester with 2-(pyrazin-2-yl)-hydrazine carboxylic acid or a pharmaceutically acceptable salt thereof.

23. The compound of claim 1 which is rapamycin 42-ester with 2-(pyrimidin-2-yl)-hydrazinecarboxylic acid or a pharmaceutically acceptable salt thereof.

24. The compound of claim 1 which is rapamycin 42-ester with 2,2-dimethyl-hydrazinecarboxylic acid or a pharmaceutically acceptable salt thereof.

25. The compound of claim 1 which is rapamycin 42-ester with (4-methyl-piperazin-1-yl)-carbamic acid or a pharmaceutically acceptable salt thereof.

26. The compound of claim 1 which is rapamycin 42-ester with 2-(pyridin-2-yl)-hydrazinecarboxylic acid or a pharmaceutically acceptable salt thereof.

27. The compound of claim 1 which is rapamycin 42-ester with 2-(benzothiazol-2-yl)-hydrazinecarboxylic acid or a pharmaceutically acceptable salt thereof.

28. The compound of claim 1 which is rapamycin 42-ester with 2-(quinoxalin-2-yl)-hydrazinecarboxylic acid or a pharmaceutically acceptable salt thereof.

29. The compound of claim 1 which is rapamycin 42-ester with (ethoxycarbonyl)-hydrazinecarboxylic acid or a pharmaceutically acceptable salt thereof.

30. The compound of claim 1 which is rapamycin 42-ester with 2-(4-sulfamoylphenyl)-hydrazinecarboxylic acid or a pharmaceutically acceptable salt thereof.

31. A method of treating or inhibiting transplantation rejection or graft versus host disease in a mammal which comprises administering to said mammal an antirejection effective amount of a compound of the structure

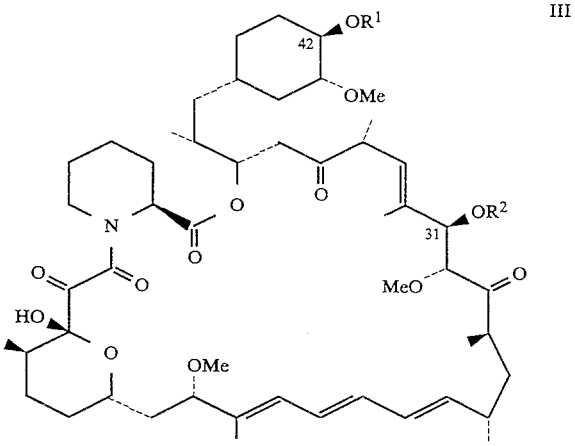

III wherein $R^1$ and $R^2$ are each, independently, hydrogen, —CONH—A—$(CR^5R^6)_n$—B, —CONR$^{11}$—A—$(CR^5R^6)_n$—B,

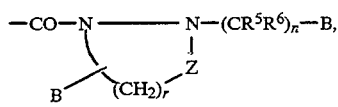

or 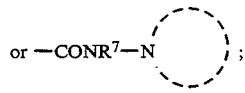 ;

$R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —$OR^7$, —$SR^7$, halogen, —CN, —$NO_2$, —$CF_3$, —$COR^7$, —$CO_2R^7$, —$CONHR^7$, —$SO_2R^7$, —$OSO_3R^7$, —$NR^7R^8$, —$NHCOR^7$, —$NHSO_2R^7$, —$SO_2NR^7R^8$, or Ar;

$R^7$ and $R^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^{11}$ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —$NR^7$—, —NHCO—, —N=C—, or —NHSO—;

Z is —$CH_2$— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3,-dihydroisobenzofuran-5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —$SO_3H$, and —$CO_2H$;

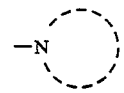

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, and —$CO_2H$;

n=0–6;

r=1–4;

with the proviso that $R^1$ and $R^2$ are not both hydrogen and further provided that when n=0, B is not —$NR^7R^8$, —$NHCOR^7$, —N=C—, or —$NHSO_2R^7$; or a pharmaceutically acceptable salt thereof.

32. A method of treating restenosis in a mammal which comprises administering to said mammal an antrestenosis effective amount of a compound having the structure

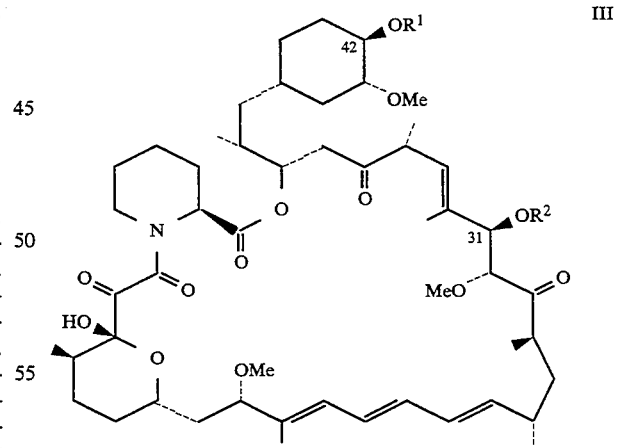

III wherein $R^1$ and $R^2$ are each, independently, hydrogen, —CONH—A—$(CR^5R^6)_n$—B, —CONR$^{11}$—A—$(CR^5R^6)_n$—B,

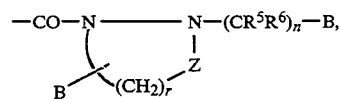

or —CONR⁷—N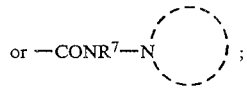;

R⁵, R⁶, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —OR⁷, —SR⁷, halogen, —CN, —NO₂, —CF₃, —COR⁷, —CO₂R⁷, —CONHR⁷, —SO₂R⁷, —OSO₃R⁷, —NR⁷R⁸, —NHCOR⁷, —NHSO₂R⁷—SO₂NR⁷, R⁸, or Ar;

R⁷ and R⁸ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

R¹¹ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —NR⁷—, —NHCO—, —N=C—, or —NHSO—;

Z is —CH₂— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3, -dihydroisobenzofuran- 5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —SO₃H, and —CO₂H;

—N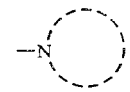

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, and —CO₂H;

n = 0–6;

r = 1–4;

with the proviso that R¹ and R² are not both hydrogen and further provided that when n=0, B is not —NR⁷R⁸, —NHCOR⁷, —N=C—, or —NHSO₂R⁷; or a pharmaceutically acceptable salt thereof.

33. A method of treating rheumatoid arthritis in a mammal which comprises administering to said mammal an antiarthritis effective amount of a compound of the structure

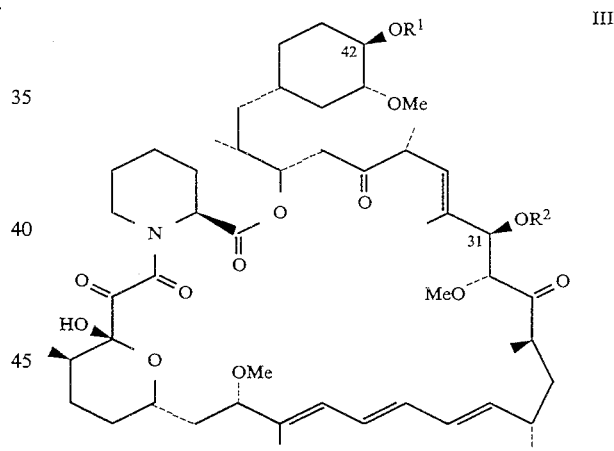

III wherein R¹ and R² are each, independently, hydrogen, —CONH—A—(CR⁵R⁶)ₙ—B, —CONR¹¹—A—(CR⁵R⁶)ₙ—B

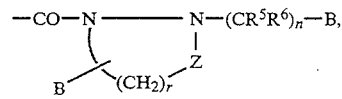

or —CONR⁷—N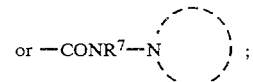;

R⁵, R⁶, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —OR⁷, —SR⁷, halogen, —CN, —NO₂, —CF₃, —COR⁷, —CO₂R⁷, —CONHR⁷, —SO₂R⁷, OSO₃R⁷, —NR⁷R⁸, —NHCOR⁷, —NHSO₂R⁷, —SO₂NR⁷R⁸, or Ar;

R⁷ and R⁸ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

R¹¹ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —NR⁷—, —NHCO—, —N=C—, or —NHSO—;

Z is —CH₂— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3,-dihydroidobenzofuran-5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —SO₃H, and —CO₂H;

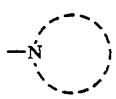

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, and —CO₂H;

n=0–6;

r=1–4;

with the proviso that R¹ and R² are not both hydrogen and further provided that when n=0, B is not —NR⁷R⁸, —NHCOR⁷, —N=C—, or —NHSO₂R⁷; or a pharmaceutically acceptable salt thereof.

34. A method of treating asthma in a mammal which comprises administering to said mammal an antiasthma effective amount of a compound of the structure

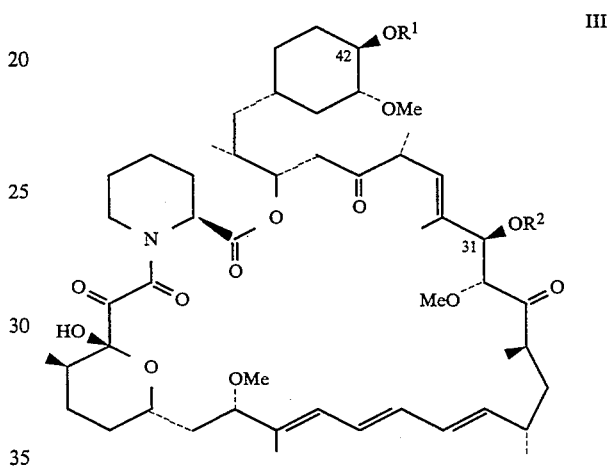

wherein R¹ and R² are each, independently, hydrogen, —CONH—A—(CR⁵R⁶)ₙ—B, —CONR¹¹—A—(CR⁵R⁶)ₙ—B,

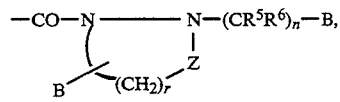

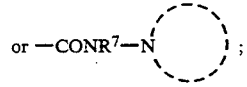

R⁵, R⁶, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —OR⁷, —SR⁷, halogen, —CN, —NO₂, —CF₃, —COR⁷, —CO₂R⁷, —CONHR⁷, —SO₂R⁷, —OSO₃R⁷, —NR⁷R⁸, —NHCOR⁷, —NHSO₂R⁷, —SO₂NR⁷R⁸, or Ar;

R⁷ and R⁸ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^{11}$ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —$NR^7$—, —NHCO—, —N=C—, or —NHSO—;

Z is —$CH_2$— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3,-dihydrosiobenzofuran-5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —$SO_3H$, and —$CO_2H$;

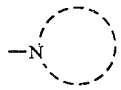

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, and —$CO_2H$;

n=0–6;
r=1–4;

with the proviso that $R^1$ and $R^2$ are not both hydrogen and further provided that when n=0, B is not —$NR^7R^8$, —$NHCOR^7$, —N=C—, or —$NHSO_2R^7$; or a pharmaceutically acceptable salt thereof.

35. A method of treating fungal infection in a mammal which comprises administering to said mammal an antifungal effective amount of a compound of the structure

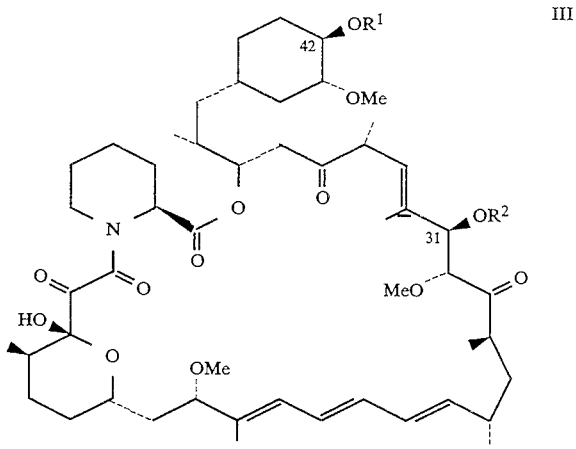

wherein $R^1$ and $R^2$ are each, independently, hydrogen, —CONH—A—$(CR^5R^6)_n$—B, —$CONR^{11}$—A—$(CR^5R^6)_n$—B,

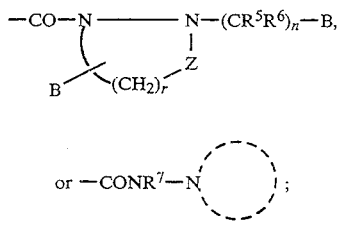

$R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —$OR^7$, —$SR^7$, halogen,—CN, —$NO_2$, —$CF_3$, —$COR^7$, —$CO_2R^7$, —$CONHR^7$, —$SO_2R^7$, —$OSO_3R^7$, —$NR^7R^8$, —$NHCOR^7$, —$NHSO_2R^7$, —$SO_2NR^7R^8$, or Ar;

$R^7$ and $R^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^{11}$ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —NR$^7$—, —NHCO—, —N=C—, or —NHSO—;

Z is —CH$_2$— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3, -dihydroisobenzofuran- 5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —SO$_3$H, and —CO$_2$H;

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H;

n=0–6;
r=1–4;

with the proviso that R$^1$ and R$^2$ are not both hydrogen and further provided that when n=0, B is not —NR$^7$R$^8$, —NHCOR$^7$, —N=C—, or —NHSO$_2$R$^7$; or a pharmaceutically acceptable salt thereof.

36. A pharmaceutical composition comprising a compound of the structure

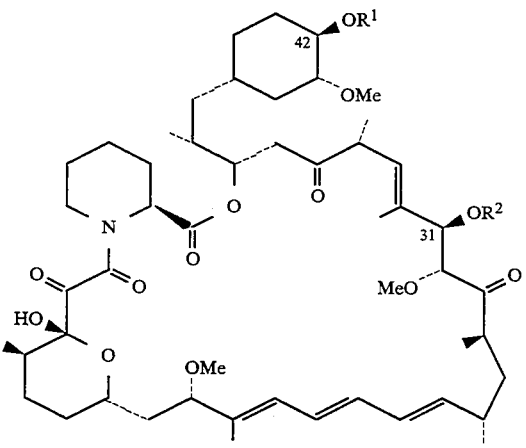

wherein R$^1$ and R$^2$ are each, independently, hydrogen, —CONH—A—(CR$^5$R$^6$)$_n$—B, —CONR$^{11}$—A—(CR$^5$R$^6$)$_n$—B,

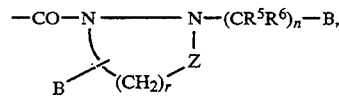

or —CONR$^7$—N

R$^5$, R$^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —OR$^7$, —SR$^7$, halogen, —CN, —NO$_2$, —CF$_3$, —COR$^7$, —CO$_2$R$^7$, —CONHR$^7$, —SO$_2$R$^7$, —OSO$_3$R$^7$, —NR$^7$R$^8$, —NHCOR$^7$, —NHSO$_2$R$^7$, —SO$_2$NR$^7$R$^8$, or Ar;

R$^7$ and R$^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

R$^{11}$ is alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

A is —NR$^7$—, —NHCO—, —N=C—, or —NHSO—;

Z is —CH$_2$— or

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, 3-oxo-1,3,-dihydroisobenzofuran-5-yl, indolyl, thiazolyl, isoxazolyl, pyrimidinyl, pyrazinyl, pyridazinyl, 1,2,4-triazinyl, 1,3,5-triazinyl, phthalazinyl, mycophenolyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, alkylcarbonyl of 2–7 carbon atoms, carbamyl, alkylcarbamyl of 2–7 carbon atoms, dialkylcarbamyl of 3–13 carbon atoms, aminosulfonyl, alkylaminosulfonyl of 1–6 carbon atoms, dialkylaminosulfonyl of 2–12 carbon atoms, arylaminosulfonyl, alkylsulfonyl of 1–6 carbon atoms, arylsulfonyl, —SO$_3$H, and —CO$_2$H;

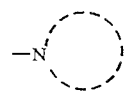

is a nitrogen containing heterocyclic radical selected from the group consisting of piperidinyl, piperazinyl, morpholinyl, pyrrolidinyl, or imidazolyl, that may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, and —CO$_2$H;

n=0–6;

r=1–4;

with the proviso that $R^1$ and $R^2$ are not both hydrogen and further provided that when n=0, B is not —NR$^7$R$^8$, —NHCOR$^7$, —N=C—, or —NHSO$_2$R$^7$; or a pharmaceutically acceptable salt thereof.

* * * * *